(12) United States Patent
Lobb et al.

(10) Patent No.: US 7,176,184 B2
(45) Date of Patent: Feb. 13, 2007

(54) TREATMENT FOR INFLAMMATORY BOWEL DISEASE WITH A FIBRONECTIN POLYPEPTIDE

(75) Inventors: Roy R. Lobb, Westwood, MA (US); Linda C. Burkly, West Newton, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 543 days.

(21) Appl. No.: 10/252,978

(22) Filed: Sep. 23, 2002

(65) Prior Publication Data

US 2003/0095969 A1    May 22, 2003

Related U.S. Application Data

(63) Continuation of application No. 09/157,452, filed on Sep. 21, 1998, now Pat. No. 6,482,409, which is a continuation of application No. 08/950,660, filed on Oct. 15, 1997, now Pat. No. 5,932,214, which is a continuation of application No. 08/456,124, filed on May 31, 1995, now abandoned, which is a continuation-in-part of application No. 08/373,857, filed on Jan. 18, 1995, now abandoned, which is a continuation-in-part of application No. 08/284,603, filed on Aug. 11, 1994, now abandoned, and a continuation-in-part of application No. PCT/US93/00924, filed on Feb. 2, 1993, which is a continuation-in-part of application No. 07/835,139, filed on Feb. 12, 1992, now abandoned.

(51) Int. Cl.
*A61K 38/04* (2006.01)
*C07K 7/00* (2006.01)

(52) U.S. Cl. .................. 514/17; 514/2; 514/8; 530/300; 530/330; 530/350

(58) Field of Classification Search ..................... None
See application file for complete search history.

(56) References Cited

U.S. PATENT DOCUMENTS

| | | |
|---|---|---|
| 4,816,397 A | 3/1989 | Boss et al. |
| 4,833,092 A | 5/1989 | Gevsen |
| 5,217,870 A | 6/1993 | Hession et al. |
| 5,272,263 A | 12/1993 | Hession et al. |
| 5,367,056 A | 11/1994 | Hession et al. |
| 5,591,719 A * | 1/1997 | Furcht et al. .................. 514/13 |
| 6,252,043 B1 | 6/2001 | Hession et al. |

FOREIGN PATENT DOCUMENTS

| | | |
|---|---|---|
| EP | 0 314 863 | 5/1989 |
| EP | 0 330 506 | 9/1989 |
| EP | 0 333 517 | 9/1989 |
| EP | 0 346 078 | 12/1989 |
| WO | WO 90/03400 | 4/1990 |
| WO | WO 90/13300 | 11/1990 |
| WO | WO 91/03252 | 3/1991 |
| WO | WO 92/00751 | 1/1992 |
| WO | WO 92/14757 | * 9/1992 |
| WO | WO 93/15764 | * 8/1993 |
| WO | WO 95/19790 | 7/1995 |

OTHER PUBLICATIONS

Albelda et al., FASEB Journal 8: 504-512, 1994.
Brown, Jr., P. et al., "Anti-Tac-H, a Humanized Antibody to the Interleukin 2 Receptor, Prolongs Primate Cardiac Allograft Survival", *Proc. Natl. Acad. Sci. USA*, 88:2663-2667 (1990).
Burkly, L. et al., "Signalling by Vascular Cell Adhesion Molecule-1 (VCAM-1) Through VLA-4 Promotes CD3-dependent T Cell Proliferation", *Eur. J. Immunol.*, 21:2871-2875 (1991).
Clackson, T. et al., "Making Antibody Fragments Using Phage Display Libraries", *Nature*, 352:624-628 (1991).
Co, M.S. et al., "Humanized Antibodies for Antiviral Therapy", *Proc. Natl. Acad. Sci. USA*, 88:2869-2873 (1990).
Damle, N. et al., "Vascular Cell Adhesion Molecule 1 Induces T-cell Antigen Receptor-dependent Activation of $CD4^+$ Lymphocytes", *Proc. Natl. Acad. Sci. USA*, 88:6403-6407 (1991).
Devlin, J. et al., "Random Peptide Libraries: A Source of Specific Protein Binding Molecules", *Science*, 249:400-406 (1990).
Dobrina, A. et al., "Mechanisms of Eosinophil Adherence to Cultured Vascular Endothelial Cells", *J. Clin. Invest.*, 88:20-26 (1991).
Edgington, Biotechnology 10: 383-389, 1992.
Elices, M.J. et al., "VCAM-1 on Activated Endothelium Interacts with the Leukocyte Integrin VLA-4 at a Site Distinct from the VLA-4/Fibronectin Binding Site", *Cell*, 60:577-584 (1990).
Freedman, A. et al., "Adhesion of Human B Cells to Germinal Centers in Vitro Involves VLA-4 and INCAM-110", *Science*, 249:1030-1033 (1990).
Harris, W.J. and S. Emery, "Therapeutic antibodies—the coming of age", *TIBTECH*, 11:42-44 (1993).
Hemler, M.E. et al., "Characterization of the Cell Surface Heterodimer VLA-4 and Related Peptides", *J. Biol. Chem.*, 262(24):11478-11485 (1987).
Holzmann, B. and I.L. Weissman, "Integrin Molecules Involved in Lymphocyte Homing to Peyer's Patches", *Immunolical Reviews*, 0(108):45-61 (1989).
Holzmann, B. et al., "Identification of a Murine Peyer's Patch-Specific Lymphocyte Homing Receptor as an Integrin Molecule with an α Chain Homologous to Human VLA-4α", *Cell*, 56:37-46 (1989).
Issekutz, T., "Inhibition of In Vivo Lymphocyte Migration to Inflammation and Homing to Lymphoid Tissues by the TA-2 Monoclonal Antibody", *J. Immunol.*, 147:4178-4184 (1991).
Jakubowski et al., "Vascular Cell Adhesion Molecule (VCAM)-1g Fusion Protein Defines Distinct Affinity States of the Very Late Antigen-4 (VLA-4) Receptor", *Cell Adhesion and Communications*, 3:131-142 (1995).

(Continued)

*Primary Examiner*—Phillip Gambel
(74) *Attorney, Agent, or Firm*—Fish & Richardson P.C.

(57) ABSTRACT

A method for the treatment of inflammatory bowel disease (IBD) is disclosed. The method comprises administration of an antibody, polypeptide or other molecule recognizing VLA-4, a surface molecule expressed on most types of white blood cells and involved in leukocyte adhesion to endothelium and other tissues in the gut.

9 Claims, 8 Drawing Sheets

OTHER PUBLICATIONS

Jones et al., Gut 36: 724-730, 1995.

Jones, P.T. et al., "Replacing the Complementarity-Determining Regions in a Human Antibody with Those From a Mouse", *Nature*, 321:522-525 (1986).

Jutila, M.A. et al., "Homing Receptors in Lymphocyte, Neutrophil, and Monocyte Interaction with Endothelial Cells" in *Leukocyte Adhesion Molecules*, T.A. Springer et al. (eds) (New York: Springer-Verlag New York Inc., 1990) Chp. 17, 227-235.

Kilshaw, P. and S.J. Murant, "Expression and Regulation of $\beta_7$-($\beta$p) Integrins on Mouse Lymphocytes: Relevance to the Mucosal Immune System", *Eur. J. Immunol.*, 21:2591-2597 (1991).

KÖhler, G. and C. Milstein, "Continuous Cultures of Fused Cells Secreting Antibody of Predefined Specificity", *Nature*, 265:495-497 (1975).

Koizumi, M. et al., "Expression of Vascular Adhesion Molecules in Inflammatory Bowel Disease", *Gastroent.*, 103:840-847 (1992).

Lichtiger, S. and D.H. Present, "Preliminary Report: Cyclosporin in Treatment of Severe Active Ulcerative Colitis", *Lancet*, 336:16-19 (1990).

Lobb, R. et al., "Expression and Functional Characterization of a Soluble Form of Vascular Cell Adhesion Molecule 1", *Biochem. Biophys. Res. Commun.*, 178(3):1498-1504 (1991).

Lobb, R. et al., "Expression and Functional Characterization of a Soluble Form of Endothelial-Leukocyte Adhesion Molecule", *J. Immunol.*, 147(1):124-129 (1991).

Lobb, R. et al., "Vascular Cell Adhesion Molecule-1", in *Cellular and Molecular Mechanisms of Inflammation: Vascular Adhesion Molecules*, vol. 2, C.G. Cochrane and M.A. Gimbrone, Jr. (eds.) (New York: Academic Press Inc., 1991) Chp. 8, 151-169.

Madara, J. et al., "Characterization of Spontaneous Colitis in Cotton-Top Tamarin (*Saguinus oedipus*) and Its Response to Sulfasalazine", *Gastroent.*, 88:13-19 (1985).

Malizia, G. et al., "Expression of Leukocyte Adhesion Molecules by Mucosal Mononuclear Phagocytes in Inflammatory Bowel Disease", *Gastroent.*, 100:150-159 (1991).

Osband, M.E. and S. Ross, "Problems in the Investigational Study and Clinical Use of Cancer Immunotherapy", *Immunol. Today*, 11:193-195 (1990).

Osborn, L., "Leukocyte Adhesion to Endothelium in Inflammation", *Cell*, 62:3-6 (1990).

Osborn, L. et al., "Direct Expression Cloning of Vascular Cell Adhesion Molecule I, a Cytokine-induced Endothelial Protein That Binds to Lymphocytes", *Cell*, 59:1203-1211 (1989).

Podolsky, D.K., "Colonic Glycoproteins in Ulcerative Colitis: Potentials Meaning in Heterogeneity", *Inflammatory Bowel Diseases: Basic Research and Clinical Implications*, Falk Symposium, Titisee, Germany, Jun. 7-9, 1987 (Boston, MA: Kluwer Academic Publishers, 1987) pp. 49-56.

Podolsky, D.K. and D.A. Fournier, "Alterations in Mucosal Content of Colonic Glycoconjugates in Inflammatory Bowel Disease Defined by Monoclonal Antibodies", *Gastroent.*, 95:379-387 (1988).

Podolsky, D.K. and D.A. Fournier, "Emergence of Antigenic Glycoprotein Structures in Ulcerative Colitis Detected Through Monoclonal Antibodies", *Gastroent.*, 95:371-378 (1988).

Podolsky, D.K. et al., "Attenuation of Colitis in the Cotton-top Tamarin by Anti-α4 Integrin Monoclonal Antibody", *J. Clin. Invest.*, 92:372-380 (1993).

Podolsky, D.K. et al., "Colonic Mucin Composition in Primates Selective Alterations Associated with Spontaneous Colitis in the Cotton-top Tamarin", *Gastroent.*, 88:20-25 (1985).

Podolsky, D.K. et al., "Spontaneous Colitis in Cotton-Top Tamarins: Histologic, Clinical and Biochemical Features of an Animal Model of Chromic Colitis", *Digestive Diseases and Sciences*, 30(4):396 (A-32) (1985).

Pulido, R. et al., "Functional Evidence for Three Distinct and Independently Inhibitable Adhesion Activities Mediated by the Human Integrin VLA-4", *J. Biol. Chem.*, 266(16):10241-10245 (1991).

Rice, G.E. et al., "Vascular and Nonvascular Expression of INCAM-110", *Am. J. Pathology*, 138(2):385-393 (1991).

Riechmann, L. et al., "Reshaping Human Antibodies for Therapy", *Nature*, 332:323-327 (1988).

Salmi, M. and S. Jalkanen, "Regulation of Lymphocyte Traffic to Mucosa-Associated Lymphatic Tissues" *Gastroent. Clin. N. Am.*, 20(3):495-510 (1991).

Sanchez-Madrid, F. et al., "VLA-3: A novel polypeptide association within the VLA molecular complex: cell distribution and biochemical characterization", *Eur. J. Immunol.*, 16:1343-1349 (1986).

Scott, J.K. and G.P. Smith, "Searching for Peptide Ligands with an Epitope Library", *Science*, 249:386-390 (1990).

Sherman-Gold, R., "Companies Pursue Therapies Based on Complex Cell Adhesion Molecules", *Genetic Engineering News*, 13:6-7, 14 (1993).

Soriano et al., Laboratory investigation 80: 1541-1551, 2000.

Springer, T.A., "Adhesion Receptors of the Immune System", *Nature*, 346:425-434 (1990).

Steiner, J. and J. Grindley, "Phase II Clinical Trial Results—Too Many Expectations?", *Bio/Technology*, 11:644 (1993).

Stoolman, L.M., "Adhesion Molecules Controlling Lymphocyte Migration", *Cell*, 56:907-910 (1989).

Taichman, D.B. et al., "Tumor Cell Surface $\alpha^4\beta_1$ Integrin Mediates Adhesions to Vascular Endothelium: Demonstration of an Interaction with the N-Terminal Domains of INCAM-110/VCAM-1", *Cell-Regulation*, 2:347-355 (1991).

van Seventer, G.A. et al., "Analysis of T Cell Stimulation by Superantigen Plus Major Histocompatibility Complex Class II Molecules or by CD3 Monoclonal Antibody: Costimulation by Purified Adhesion Ligands VCAM-1, ICAM-1, but Not ELAM-1", *J. Exp. Med.*, 174:901-913 (1991).

Waldmann, T.A., "Monoclonal Antibodies in Diagnosis and Therapy", *Science*, 252:1657-1662 (1991).

Ward, E.S. et al., "Binding Activities of a Repertoire of Single Immunoglobulin Variable Domains Secreted From *Escherichia coli*", *Nature*, 341:544-546(1989).

Ward et al., Therapeutic Immunol. 1: 165-171, 1994.

Weller, P.F. et al., "Human Eosinophil Adherence to Vascular Endothelium Mediated by Binding to Vascular Cell Adhesion Molecule 1 and Endothelial Leukocyte Adhesion Molecule 1", *Proc. Natl. Acad. Sci. USA*, 88: 7430-7433 (1991).

Yuan, Q. et al., "Cloning and Sequence Analysis of a Novel $\beta_2$-Related Integrin Transcript from T Lympho- cytes: Homology of Integrin Cysteine-Rich Repeats to Domain III of Laminin-B Chains", *Int'l Immunol.*, 2(11):1097-1108 (1990.

\* cited by examiner

TREATMENT FOR INFLAMMATORY BOWEL DISEASE WITH A FIBRONECTIN POLYPEPTIDE

This application is a continuation of application Ser. No. 09/157,452, filed Sep. 21, 1998, now U.S. Pat. No. 6,482,409, which is a continuation of application Ser. No. 08/950,660, filed Oct. 15, 1997, now U.S. Pat. No. 5,932,214, which is a file wrapper continuation of application Ser. No. 08/456,124, filed May 31, 1995, now abandoned, which is a continuation-in-part of Lobb U.S. Ser. No. 08/373,857, filed Jan. 18, 1995, now abandoned, which is a continuation-in-part of Lobb U.S. Ser. No. 08/284,603, filed Aug. 11, 1994, now abandoned, and of PCT/US93/00924 filed Feb. 2, 1993, which is the continuation-in-part of Lobb U.S. Ser. No. 07/835,139, filed Feb. 12, 1992, now abandoned, all of which are incorporated by reference.

FIELD OF THE INVENTION

The present invention relates to a treatment for inflammatory bowel disease (IBD). More particularly, this invention relates to the use of antibodies recognizing the integrin VLA-4 (very late antigen-4) in the treatment of IBD.

BACKGROUND OF THE INVENTION

Inflammatory bowel disease, or IBD, is a collective term encompassing ulcerative colitis and Crohn's disease (ileitis), which are chronic inflammatory disorders of the gastrointestinal tract. Ulcerative colitis is confined to the large intestine (colon) and rectum, and involves only the inner lining of the intestinal wall. Crohn's disease may affect any section of the gastrointestinal tract (i.e., mouth, esophagus, stomach, small intestine, large intestine, rectum and anus) and may involve all layers of the intestinal wall. Both diseases are characterized by abdominal pain and cramping, diarrhea, rectal bleeding and fever. The symptoms of these diseases are usually progressive, and sufferers typically experience periods of remission followed by severe flareups.

IBD affects an estimated two million people in the United States alone. Although IBD is not considered a fatal illness, prolonged disease can lead to severe malnutrition affecting growth or to the formation of abscesses or intestinal scar tissue, leading in turn to infection or bowel obstruction.

IBD has no cure, and the exact causes of IBD are not yet understood. Conventional treatments for IBD have involved anti-inflammatory drugs, immunosuppressive drugs and surgery. Sulfasalazine and related drugs having the bioactive 5-amino-salicylic acid (5-ASA) moiety are widely used to control moderate IBD symptoms and to maintain remission. Severe inflammation is often treated with powerful corticosteroids and sometimes ACTH or with immunosuppressants such as 6-mercaptopurine and azathioprine. The most common surgical treatments for severe chronic IBD are intestinal resections and, ultimately, colectomy, which is a complete cure only for ulcerative colitis.

Severe side effects are associated with the drugs commonly prescribed for IBD, including nausea, dizziness, changes in blood chemistry (including anemia and leukopenia), skin rashes and drug dependence; and the surgical treatments are radical procedures that often profoundly alter the everyday life of the patient. Accordingly, there is a great need for treatments for IBD that are effective yet less severe in their side effects and are less invasive of the IBD sufferer's body and quality of life.

The search for the causes of IBD and more effective treatments has led several investigators to study diseased and normal tissue on a cellular level. This has led to observations of variations in the normal content of intestinal mucin (Podolsky, 1988 [1]) and to the observation of colonic glycoproteins that emerge only in diseased tissue (Podolsky and Fournier, 1988a [2], 1988b [3]). Researchers have observed that the cell adhesion molecule ICAM-1 is expressed at elevated levels in IBD tissue (Malizia et al., 1991 [4]). This molecule is thought to mediate leukocyte recruitment to sites of inflammation through adhesion to leukocyte surface ligands, i.e., LFA-1 (CD11a/CD18 complex) on all leukocytes and Mac-1 (CD11b/CD18) on phagocytes. (See, e.g., Springer, 1990 [5].) Because flareups of IBD are often accompanied by increased concentrations of neutrophils and lymphocytes in the intestinal submucosa, blocking of interactions between endothelial cell receptors (such as ICAM-1) and their leukocyte ligands (such as LFA-1, Mac-1) has been proposed as a treatment for IBD.

Another cell adhesion molecule, VCAM-1 (vascular cell adhesion molecule-1) is expressed on inflamed endothelium and has been shown to recognize the $\alpha_4\beta_1$ integrin, VLA-4, expressed on the surface of all leukocytes except neutrophils (Springer, 1990 [5]). VCAM-1 also has been found to be expressed constitutively in noninflamed tissue, including Peyer's patch follicular dendritic cells (Freedman et al., 1990 [6]; Rice et al., 1991 [7]). Additionally, besides mediating cell adhesion events, VCAM-1 also has recently been determined to play a costimulatory role, through VLA-4, in T cell activation (Burkly et al., 1991 [8]; Damle and Arrufo, 1991 [9]; van Seventer et al., 1991 [10]). Accordingly, further study of VCAM-1 has been taken up to investigate whether it plays a role as a regulator of the immune response as well as a mediator of adhesion in vivo.

It has now been surprisingly discovered that administering anti-VLA-4 antibody significantly reduces acute inflammation in a primate model for IBD. Cotton top tamarins suffering from a spontaneous intestinal inflammation comparable to ulcerative colitis in humans that were treated with an anti-VLA-4 antibody (HP1/2) showed significant reduction in inflammation of biopsied intestinal tissue.

SUMMARY OF THE INVENTION

Accordingly, the present invention provides novel methods for the treatment of IBD and further provides new pharmaceutical compositions useful in the treatment of IBD. In particular, the present invention provides a method comprising the step of administering to an IBD sufferer a VLA-4 blocking agent, e.g., an anti-VLA-4 antibody, such as antibody HP1/2 Also contemplated is the use of analogous antibodies, antibody fragments, soluble proteins and small molecules that mimic the action of anti-VLA-4 antibodies in the treatment of IBD.

DETAILED DESCRIPTION OF THE DRAWINGS

FIG. 1 is a schematic depicting structure of VCAM 2D-IgG fusion protein described in Example V. VCAM 2D-IgG is a soluble form of the ligand for VLA4 (VCAM1) and consists of the two N-terminal domains of VCAM1 fused to the human IgG1 heavy chain constant region sequences (Hinges, $C_H2$ and $C_H3$).

FIG. 2 is graph depicting VCAM-IgG inhibitory dose response after single intraperitoneal doses in mouse contact hypersensitivity. VCAM-IgG tested over a dose range of 1.25 to 20 mg/kg (25–400 µg/mouse) maximally inhibited the mouse ear swelling response about 4/5 as well as the PS/2 antibody. Maximal inhibition occurred at the 10 mg/kg dose. The ED50 was about 2.5 mg/kg, i.p. (50 µg/mouse).

FIG. 3 is a graph depicting inhibition of the mouse ear swelling response by VCAM-IgG in mouse contact hypersensitivity. In a confirmation study, VCAM-IgG tested at 20 mg/kg i.p. (400 µg/mouse) maximally inhibited the mouse ear swelling response as effectively as the PS/28 mg/kg i.v. antibody dose.

FIG. 4 is a graph depicting the effect of VCAM 2D-IgG fusion protein and controls on prevention of diabetes after adoptive transfer of spleen cells; the frequency of recipients which became diabetic and day of disease onset are shown for transfer of $2 \times 10^7$ splenocytes from diabetic (D) NOD donors with an irrelevant rat LFA-3Ig fusion protein treatment (closed squares), and with VCAM 2D-IgG treatment (open circles) or of recipients which received PBS alone without cells transferred (closed triangles); the splenocytes were transferred with VCAM 2D-IgG or rat LFA-3Ig, and then VCAM 2D-IgG or rat LFA-3Ig was injected every other day through day 17 post-transfer (n=5 for all groups).

DETAILED DESCRIPTION OF THE INVENTION

Figure 1:
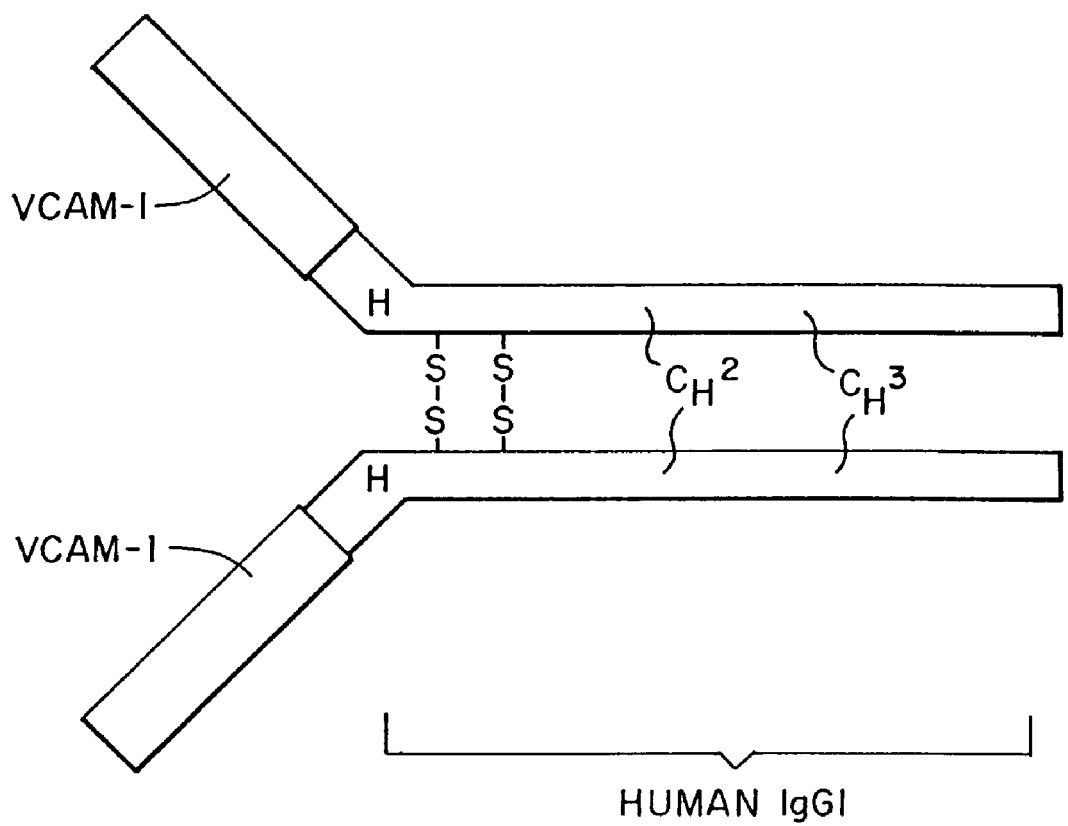

The technology for producing monoclonal antibodies is well known. Briefly, an immortal cell line (typically myeloma cells) is fused to lymphocytes (typically splenocytes) from a mammal immunized with whole cells-expressing a given antigen, e.g., VLA-4, and the culture supernatants of the resulting hybridoma cells are screened for antibodies against the antigen. (See, generally, Kohler and Milstein, 1975 [11].)

Immunization may be accomplished using standard procedures. The unit dose and immunization regimen depend on the species of mammal immunized, its immune status, the body weight of the mammal, etc. Typically, the immunized mammals are bled and the serum from each blood sample is assayed for particular antibodies using appropriate screening assays. For example, anti-VLA-4 antibodies may be identified by immunoprecipitation of $^{125}$I-labeled cell lysates from VLA-4-expressing cells. (See, Sanchez-Madrid et al., 1986 [13] and Hemler et al., 1987 [14].) Anti-VLA-4 antibodies may also be identified by flow cytometry, e.g., by measuring fluorescent staining of Ramos cells incubated with an antibody believed to recognize VLA-4 (see, Elices et al., 1990 [15]). The lymphocytes used in the production of hybridoma cells typically are isolated from immunized mammals whose sera have already tested positive for the presence of anti-VLA-4 antibodies using such screening assays.

Typically, the immortal cell line (e.g., a myeloma cell line) is derived from the same mammalian species as the lymphocytes. Preferred immortal cell lines are mouse myeloma cell lines that are sensitive to culture medium containing hypoxanthine, aminopterin and thymidine ("HAT medium"). HAT-sensitive mouse myeloma cells may be fused to mouse splenocytes, e.g., using 1500 molecular weight polyethylene glycol ("PEG 1500"). Hybridoma cells resulting from the fusion are then selected using HAT medium, which kills unfused and unproductively fused myeloma cells (unfused splenocytes die after several days because they are not transformed). Hybridomas producing a desired antibody are detected by screening the hybridoma culture supernatants. For example, hybridomas prepared to produce anti-VLA-4 antibodies may be screened by testing the hybridoma culture supernatant for secreted antibodies having the ability to bind to a recombinant $\alpha_4$-subunit-expressing cell line, such as transfected K-562 cells (see, Elices et al., [15]).

To produce anti VLA-4-antibodies, hybridoma cells that test positive in such screening assays may be cultured in a nutrient medium under conditions and for a time sufficient to allow the hybridoma cells to secrete the monoclonal antibodies into the culture medium. Tissue culture techniques and culture media suitable for hybridoma cells are well known. The conditioned hybridoma culture supernatant may be collected and the anti-VLA-4 antibodies optionally further purified by well-known methods.

Alternatively, the desired antibody may be produced by injecting the hybridoma cells into the peritoneal cavity of a mouse primed with 2,6,10,14-tetramethylpentadecane (PRISTANE; Sigma Chemical Co., St. Louis Mo.). The hybridoma cells proliferate in the peritoneal cavity, secreting the antibody, which accumulates as ascites fluid. The antibody may be harvested by withdrawing the ascites fluid from the peritoneal cavity with a syringe.

Several anti-VLA-4 monoclonal antibodies have been previously described (see, e.g., Sanchez-Madrid et al., 1986 [12]; Hemler et al. (1987) [13]; Pulido et al. (1991) [14]). For the experiments herein, an anti-VLA-4 monoclonal antibody designated HP1/2 (obtained from Biogen, Inc., Cambridge, Mass.) was used. The variable regions of the heavy and light chains of the anti-VLA-4 antibody HP1/2 have been cloned, sequenced and expressed in combination with constant regions of human immunoglobulin heavy and light chains. Such a chimeric HP1/2 antibody is similar in specificity and potency to the murine HP1/2 antibody, and may be useful in methods of treatment according to the present invention. Similarly, humanized recombinant anti-VLA-4 antibodies may be useful in these methods. The HP1/2 $V_H$ DNA sequence and its translated amino acid sequences are set forth in SEQ ID NO: 1 and SEQ ID NO: 2, respectively. The HP1/2 $V_K$ DNA sequence and its translated amino acid sequence are set forth in SEQ ID NO: 3 and SEQ ID NO: 4, respectively.

Monoclonal antibodies such as HP1/2 and other anti-VLA-4 antibodies (e.g., Mab HP2/1, HP2/4, L25, P4C2) capable of recognizing the a chain of VLA-4 will be useful in the present invention. It is most preferred that the antibodies will recognize the B1 or B2 epitopes of the VLA-$\alpha_4$ chain (see, Pulido et al. (1991) [15]). While not wishing to be bound by one scientific theory, anti-VLA-4 antibodies used according to the method of the present invention may specifically inhibit, at least for an initial period, the migration of VLA-4-expressing leukocytes to inflamed sections of the gut. Or, the release of inflammatory mediators and cytokines by leukocytes already recruited to IBD tissue may be blocked by anti-VLA-4 antibodies that prevent some form of VCAM-1-mediated signal transduction, such as the T cell co-activation observed previously (e.g., Burkly et al. 1991 [8]). Monoclonal antibody HP1/2 has been shown to block leukocyte adhesion to VCAM-1-expressing cells but not to promote VLA-4-mediated T cell activation.

The method of the present invention comprises administering to a mammal suffering from inflammatory bowel disease a composition comprising a VLA-4 blocking agent, e.g., an anti-VLA-4 antibody. The examples below set forth the results observed in cotton top tamarins. The physiological and histochemical similarities between a spontaneous chronic diffuse colitis observed in the cotton top tamarin (CTT) and IBD humans has been documented (see, e.g., Podolsky et al., 1985a [16], Podolsky et al., 1985b [17]). Prior studies have also demonstrated parallel responses in CTTs to therapeutic compounds used in the management of the human IBD (see, e.g., Madara et al., 1985 [18]). Accordingly, the results reported herein will be relevant and applicable to, and the method claimed will be useful in any mammal, including humans, suffering from IBD.

The VLA-4 blocking agent, e.g., an anti-VLA-4 antibody, administered in accordance with the present invention may be administered-prophylactically to a chronic IBD sufferer, to bring about or maintain remission of the disease; however, preferably the method of the present invention is used to treat acute flareups of the disease.

The VLA-4 blocking agent, e.g., an anti-VLA-4 antibody, can be administered in the form of a composition, e.g., a composition comprising an anti-VLA-4 antibody and a pharmaceutically acceptable carrier. Preferably, the composition will be in a form suitable for intravenous injection. For acute flareups of ulcerative colitis or Crohn's disease, dosages of antibodies from 0.05 mg/kg-patient/day to 5.0 mg/kg-patient/day (preferably from 0.5 mg/kg-patient/day to 2.0 mg/kg-patient/day) may be used, although higher or lower dosages may be indicated with consideration to the age, sensitivity, tolerance, and other characteristics of the patient, the acuteness of the flareup, the history and course of the disease, plasma level and half-life of the antibody employed and its affinity for its recognition site, and other similar factors routinely considered by an attending physician. For maintenance of remission from active disease, dosages from 0.05 mg/kg-patient/day to 5.0 mg/kg-patient/day (preferably from 0.5 mg/kg-patient/day to 2.0 mg/kg-patient/day) may be used, although higher or lower dosages may be indicated and employed with advantageous effects considering the age, sensitivity, tolerance, and other characteristics of the patient, the pattern of flareups, the history and course of the disease, the plasma level and half-life of the agent, e.g., an antibody, employed and its affinity for its recognition site, and other similar factors routinely considered by an attending physician. Dosages may be adjusted, for example, to provide a particular plasma level of an agent, e.g., an antibody, e.g., in the range of 5–30 µg/ml, more preferably 10–15 µg/ml, for murine antibodies, and to maintain that level, e.g., for a period of time (e.g., 1 week) or until clinical results are achieved (e.g., flareup subsides). Chimeric and humanized antibodies, which would be expected to be cleared more slowly, will require lower dosages to maintain an effective plasma level. Also, antibodies or fragments having high affinity for VLA-4 will need to be administered less frequently or in lower doses than antibodies or antibody fragments of lesser affinity.

Suitable pharmaceutical carriers include, e.g., sterile saline, physiological buffer solutions and the like. The pharmaceutical compositions may additionally be formulated to control the release of the active ingredients or prolong their presence in the patient's system. Numerous suitable drug delivery systems are known for this purpose and include, e.g., hydrogels, hydroxmethylcellulose, microcapsules, liposomes, microemulsions, microspheres, and the like. Phosphate buffered saline (PBS) is a preferred carrier for injectible compositions.

It will also be recognized that for the purposes of the present invention, antibodies capable of binding to the $\alpha_4$ subunit of VLA-4 should be employed. It is preferred that monoclonal antibodies be used.

In addition to naturally produced antibodies, suitable recombinant antibodies capable of binding to VLA-4 may alternatively be used. Such recombinant antibodies include antibodies produced via recombinant DNA techniques, e.g., by transforming a host cell with a suitable expression vector containing DNA encoding the light and heavy immunoglobulin chains of the desired antibody, and recombinant chimeric antibodies, wherein some or all of the hinge and constant regions of the heavy and/or the light chain of the anti-VLA-4 antibody have been substituted with corresponding regions of an immunoglobulin light or heavy chain of a different species (i.e., preferably the same species as the IBD sufferer being treated, to minimize immune response to the administered antibody). (See, e.g., Jones et al., 1986 [19], Ward et al., 1989 [20], and U.S. Pat. No. 4,816,397 (Boss et al.) [21], all incorporated herein by reference.) Recombinant antibodies specifically contemplated herein include CDR-grafted antibodies or "humanized" antibodies, wherein the hypervariable regions of, e.g., murine antibodies are grafted onto framework regions of, e.g., a human antibody. (See, e.g., Riechmann et al., 1988 [22]; Man Sung Co et al., 1991 [23]; Brown, Jr., 1991 [24].)

Furthermore, VLA-4-binding fragments of anti-VLA-4 antibodies, such as Fab, Fab', F(ab')$_2$, and F(v) fragments; heavy chain monomers or dimers; light chain monomers or dimers; and dimers consisting of one heavy chain and one light chain are also contemplated herein. Such antibody fragments may be produced by chemical methods, e.g., by cleaving an intact antibody with a protease, such as pepsin or papain, or via recombinant DNA techniques, e.g., by using host cells transformed with truncated heavy and/or light chain genes. Heavy and light chain monomers may similarly be produced by treating an intact antibody with a reducing agent such as dithiothreitol or β-mercaptoethanol or by using host cells transformed with DNA encoding either the desired heavy chain or light chain or both.

As an alternative to hybridoma technology, antibody fragments having the desired anti-VLA-4 specificities may be isolated by phage cloning methods. (See, e.g., Clackson et al., 1991 [25].)

Also, from the discussion herein it will be apparent that other VLA-4 blocking agents can be used in the methods described herein. For the purposes of the invention a VLA-4 blocking agent refers to an agent, e.g., a polypeptide or other molecule, which can inhibit or block VLA-4-mediated binding or which can otherwise modulate VLA-4 function, e.g., by inhibiting or blocking VLA-4-ligand mediated VLA-4 signal transduction and which is effective in the treatment of IBD, preferably in the same manner as are anti-VLA-4 antibodies.

A VLA-4 blocking agent is a molecule which has one or more of the following properties: (1) it coats, or binds to, a VLA-4 antigen on the surface of a VLA-4 bearing cell with sufficient specificity to inhibit a VLA-4-ligand/VLA-4 interaction, e.g., the VLA-4/VCAM-1 interaction; (2) it coats, or binds to, a VLA-4 antigen on the surface of a VLA-4 bearing cell with sufficient specificity to modify, and preferably to inhibit, transduction of a VLA-4-mediated signal, e.g., VLA-4/VCAM-1-mediated signaling; (3) it coats, or binds to, a VLA-4-ligand, e.g., VCAM-1 or fibronectin, with sufficient specificity to inhibit the VLA-4/VLA-4-ligand interaction; (4) it coats, or binds to, a VLA-4-ligand, e.g., VCAM-1 or fibronectin, with sufficient specificity to modify, and preferably to inhibit, transduction of VLA-4-ligand mediated VLA-4 signaling, e.g., VCAM-1-mediated VLA-4 signaling. In preferred embodiments the VLA-4 blocking agent has one or both of properties 1 and 2. In other preferred embodiments the VLA-4 blocking agent has one or both of properties 3 and 4.

For purposes of the invention, any agent capable of binding to VLA-4 antigens on the surface of VLA-4 bearing cells and which effectively blocks or coats VLA-4 antigens, is considered to be an equivalent of the monoclonal antibody used in the examples herein.

As discussed herein, the blocking agents used in methods of the invention are not limited to antibodies or antibody derivatives, but may be other molecules, e.g., soluble forms of other proteins which bind VLA-4, e.g., the natural binding proteins for VLA-4. These binding agents include soluble VCAM-1 or VCAM-1 peptides, VCAM-1 fusion proteins, bifunctional VCAM-1/Ig fusion proteins, fibronectin, fibronectin having an alternatively spliced non-type III connecting segment, and fibronectin peptides containing the amino acid sequence EILDV (SEQ ID NO:17) or a similar conservatively substituted amino acid sequence. These binding agents can act by competing with the cell-surface binding protein for VLA-4 or by otherwise altering VLA-4 function. For example, a soluble form of VCAM-1 (see, e.g., Osborn et al. 1989 [26]) or a fragment thereof may be administered to bind to VLA-4, and preferably compete for a VLA-4 binding site, thereby leading to effects similar to the administration of anti-VLA-4 antibodies. Soluble VCAM-1 fusion proteins can be used in the methods described herein. For example, VCAM-1, or a fragment thereof which is capable of binding to VLA-4 antigen on the surface of VLA-4 bearing cells, e.g., a fragment containing the two N-terminal domains of VCAM-1, can be fused to a second peptide, e.g., a peptide which increases the solubility or the in vivo life time of the VCAM-1 moiety. The second peptide can be a fragment of a soluble peptide, preferably a human peptide, more preferably a plasma protein, or a member of the immunoglobulin super family. In particularly preferred embodiments the second peptide is IgG or a portion or fragment thereof, e.g., the human IgG1 heavy chain constant region. A particularly preferred fusion protein is the VCAM 2D-IgG fusion.

Included in the invention as VLA-4 blocking agents are (at least) peptides (preferably peptides of less than 5 or 10 amino acid resides in length), peptide mimetics, carbohydrates, and small molecules, such as oligosaccharides, capable of blocking VLA-4 in any of the ways described herein, e.g., by binding VLA-4 antigens on the surface of VLA-4-bearing cells or by binding to VLA-4-ligands. Small molecules such as oligosaccharides that mimic the binding domain of a VLA-4 ligand and fit the receptor domain of VLA-4 may also be employed. (See, J. J. Devlin et al., 1990 [24], J. K. Scott and G. P. Smith, 1990 [25], and U.S. Pat. No. 4,833,092 (Geysen) [26], all incorporated herein by reference.) Examples of small molecules useful in the invention can be found in Adams et al. U.S. Ser. No. 08/376,372, filed Jan. 23, 1995, hereby incorporated by reference.

In preferred embodiments more than one VLA-4 blocking agent is administered to a patient, e.g., a VLA-4 blocking agent which binds to VLA-4 can be combined with a VLA-4 blocking agent which binds to VCAM-1.

The use of such VLA-4 blocking agents, e.g., VLA-4-binding polypeptides or molecules that effectively decrease inflammation in IBD tissue in treated subjects is contemplated herein as an alternative method for treatment of IBD.

It is also contemplated that anti-VLA-4 antibodies may be used in combination with other antibodies having a therapeutic effect on IBD. For instance, to the extent that the beneficial effects reported herein are due to the inhibition of leukocyte recruitment to endothelium, combinations of anti-VLA-4 antibodies with other antibodies that interfere with the adhesion between leukocyte antigens and endothelial cell receptor molecules may be advantageous. For example, in addition to the use of anti-VLA-4 antibodies in accordance with this invention, the use of anti-ELAM-1 antibodies, anti-VCAM-1 antibodies, anti-ICAM-1 antibodies, anti-CDX antibodies, anti-CD18 antibodies, and/or anti-LFA-1 antibodies may be advantageous.

When formulated in the appropriate vehicle, the pharmaceutical compositions contemplated herein may be administered by any suitable means such as orally, intraesophageally or intranasally, as well as subcutaneously, intramuscularly, intravenously, intra-arterially, or parenterally. Ordinarily intravenous (i.v.) or parenteral administration will be preferred to treat flareup conditions; oral administration in a timed release vehicle will be preferred to maintain remission.

Improvement for IBD patients as a result of the methods of this invention can be evaluated by any of a number of methods known to practitioners in this art. For example, improvement in observed symptomology such as the True-love-Witts criteria (see, e.g., Lichtiger, et al., 1990 [30]) may be used, or specimens of colon tissue may be biopsied and characterized histologically (see, e.g., Madara et al., 1985 [18]).

In another aspect the invention features a chimeric molecule which includes: (1) a VLA-4 targeting moiety, e.g., a VCAM-1 moiety capable of binding to VLA-4 antigen on the surface of VLA-4 bearing cells; (2) optionally, a second peptide, e.g., one which increases solubility or in vivo life time of the VLA-4 targeting moiety, e.g., a member of the immunoglobulin super family or fragment or portion thereof, e.g., a portion or a fragment of IgG, e.g., the human IgG1 heavy chain constant region, e.g., $C_H2$ and $C_H3$ hinge regions; and (3) a toxin moiety. The VLA-4 targeting moiety can be any naturally occurring VLA-4 ligand or fragment thereof, e.g., a VCAM-1 peptide; fibronectin, fibronectin having an alternatively spliced non-type III connecting segment, and fibronectin peptides containing the amino acid sequence EILDV (SEQ ID NO:17) or a similar conservatively substituted amino acid sequence. A preferred targeting moiety is a soluble VCAM-1 fragment, e.g., the N-terminal domains 1 and 2 of the VCAM-1 molecule. The toxin moiety can be any agent which kills or inactivates a cell when the toxin is targeted to the cell by the VLA-4 targeting moiety. Toxin moieties include: cytotoxic peptide moieties, e.g., Diphtheria toxin A, *Pseudomonas* Exotoxin, Ricin A, Abrin A, *Schigella* toxin, or Gelonin; radionucleotides; and chemotherapeutic agents.

The chimeric molecule can be used to treat a subject, e.g., a human, at risk for a disorder, e.g., IBD, characterized by the presence of cells bearing VLA-4, and preferably activated VLA-4.

The methods and compositions of the present invention will be further illuminated by reference to the following examples, which are presented by way of illustration and not of limitation.

EXAMPLE I

VCAM1 Expression in the Colon

Experiments were performed to determine whether active IBD involved the expression of endothelial cell surface proteins involved in leukocyte adhesion. Expression of VCAM-1 in colon tissue of IBD sufferers and normal or uninvolved colon tissue controls was evaluated. Human colonoscopic biopsy tissue samples were obtained, with informed consent, and prepared as frozen sections by mounting in OCT compound (TissueTek) and quick freezing in isopentane/liquid nitrogen. The human colon samples were from normal colon, active ulcerative colitis colon (UC-active), inactive ulcerative colitis colon (UC-inactive), uninvolved ulcerative colitis colon (UC-uninvolved), active Crohn's Disease colon (CD-active), and uninvolved Crohn's Disease colon (CD-uninvolved).

Frozen sections (~4μ) were placed on gelatin-coated slides (1% gelatin, heated at 60° C. for 1–2 min., air dried, 1% formaldehyde at room temp., air dried), air dried 30 minutes, fixed in acetone for ten minutes at 4° C., washed three times in PBS and treated with 0.3% $H_2O_2$ in methanol (30 min., room temp.). The slides were then washed with PBS for 30 minutes, incubated with dilute normal human serum (1:100), and incubated with anti-VCAM-1 antibody 4B9 (1:100; obtained as a gift from Dr. John Harlan) for 60 minutes at room temperature. Control slides were incubated with an anti-bovine serum albumin (anti-BSA) antibody (Sigma Chemical Co., St. Louis Mo.). The samples were then washed with PBS for 10 minutes and incubated with a secondary biotinylated rabbit anti-mouse immunoglobulin (Dako Corp., Santa Barbara, Calif.) for 60 minutes at room temperature, then visualized using avidin-linked peroxidase (VECTASTAIN, Vector Labs, Burlingame Calif.).

The results of these tests are set forth in the following TABLE I:

TABLE I

Endothelial Cell Staining In Human Tissue

| Tissue (n) | VCAM-1 Expression | |
| --- | --- | --- |
| | n | (%) |
| Normal (11) | 6 | (54.4) |
| UC active (23) | 14 | (60.9) |
| UC inactive (8) | 5 | (62.5) |
| UC uninvolved (10) | 4 | (40.0) |
| CD active (9) | 5 | (55.5) |
| CD uninvolved (12) | 7 | (58.3) |

These data confirm the observations such as those reported by Freedman et al. [6] and Rice et al. [7] that VCAM-1 is expressed in both IBD-involved colon tissue and in normal colon tissue. In both CD and UC tissues, VCAM-1 was observed by immunocytochemistry in about 60% of samples.

EXAMPLE II

Anti-VLA-4 Antibody Recognition of CTT White Blood Cells

An anti-VLA-4 monoclonal antibody (HP1/2, obtained from Biogen, Inc., Cambridge Mass.) was tested to confirm that it recognized an epitope on CTT leukocytes.

Blood samples (3 ml) from CTTs were heparinized and the CTT peripheral blood mononuclear leukocytes (PBLs) were isolated using a Ficoll-Hypaque gradient (Pharmacia) according to the manufacturer's instructions for isolation of human PBLs. CTT PBLs were examined for their ability to bind to the murine anti-human VLA-4 monoclonal antibodies HP1/2 and HP2/1 by FACS analysis using a Becton Dickenson FACStar and standard techniques (see, e.g., Lobb et al., 1991a [31]). Both monoclonal antibodies bound to CTT PBLs, indicating that both human and CTT VLA4 have similar epitopes recognized by these two antibodies.

CTT PBLs were also observed to adhere to microtiter plates coated with immobilized recombinant soluble human VCAM-1 (Biogen, Inc.), which binding was blocked by HP1/2 and HP2/1. These results show that CTT PBLs bind to VCAM-1 in a VLA-4-dependent manner, and that HP1/2 and HP2/1 block the interaction of CTT VLA-4 with human VCAM-1. (Cf. Lobb et al., 1991b [32].)

EXAMPLE III

Cotton Top Tamarin Trials

A stock solution in sterile saline of the Anti-VLA-4 antibody, HP1/2 (IgG1), and a placebo control (saline only), were prepared for administration to ten cotton top tamarins (CTTs) exhibiting symptoms of spontaneous colitis (i.e., diarrhea, etc.; see, Madara et al. [18]). Five CTTs received HP1/2 and five received placebo, by intravenous injection. The CTTs receiving HP1/2 were injected with 1 mg HP1/2 per day (i.e., about 2 mg/kg/day, based on approximate half-kilogram weight of a CTT) for eight days (on Days 0, 1, 2, 3, 4, 5, 6, and 7 of the trial). Colon tissue samples obtained from the animals were biopsied every other day (on Days 0, 2, 4, 6, 8, and 10 of the trial).

Data from the biopsies were used to determine an acute inflammation index for each animal, giving a semi-quantitative analysis of the course of the colitis. (See, Madara et al. [18].) The inflammation indices before the trial began (Day 0) and at the end of the trial at Day 10 are set forth in Table II, below: ("Treated CTTs" received antibody-HP1/2; "Control CTTs" received placebo)

TABLE II

| | Day 0 AII* | Day 10 AII |
| --- | --- | --- |
| Treated CTTs | | |
| 1 | 2 | 0 |
| 2 | 1 | 0 |
| 3 | 1 | 0 |
| 4 | 2 | 0 |
| 5 | 2 | 1 |
| MEAN | 1.6 | 0.2 |

TABLE II-continued

|  | Day 0 AII* | Day 10 AII |
| --- | --- | --- |
| Control CTTs |  |  |
| C1 | 2 | 0 |
| C2 | 2 | 1 |
| C3 | 1 | 1 |
| C4 | 2 | 2 |
| C5 | 2 | 2 |
| MEAN | 1.8 | 1.2 |

*AII = acute inflammation index

These results show that treatment with anti-VLA4 antibody resulted in a significant (p<0.01) decrease in acute inflammation index.

EXAMPLE IV

The trial described in Example III was repeated using 14 CTTs, 7 receiving HP1/2 and 7 receiving placebo. The change in acute inflammation index from Day 0 to Day 10 is set forth in Table III:

TABLE III

|  | Day 0 AII | Day 10 AII |
| --- | --- | --- |
| Treated CTTs |  |  |
| 6 | 2 | 0 |
| 7 | 2 | 0 |
| 8 | 2 | 0 |
| 9 | 2 | 0 |
| 10 | 2 | 0 |
| 11 | 2 | 1 |
| 12 | 2 | 2 |
| MEAN | 2.0 | 0.43 |
| Control CTTs |  |  |
| C6 | 2 | 2 |
| C7 | 2 | 2 |
| C8 | 1 | 1 |
| C9 | 2 | 1 |
| C10 | 2 | 1 |
| C11 | 2 | 0 |
| C12 | 1 | 0 |
| MEAN | 1.71 | 1.00 |

The foregoing results show a significant decrease in acute inflammation in the CTTs receiving HP1/2.

EXAMPLE V

VCAM 2D-IgG is a soluble form of the ligand for VLA4 (VCAM1) which consists of the two N-terminal domains of VCAM1 fused to the human IgG1 heavy chain constant region sequences (Hinges, $C_H2$ and $C_H3$). The VCAM 2D-IgG DNA sequence and its translated amino acid sequence are shown in SEQ ID NO: 5 and SEQ ID NO: 12, respectively. In other systems, administration of this fusion peptide has been shown to have effects which are similar to the administration of anti-VLA-4 monoclonal antibody. FIG. 1 illustrates the fusion protein structure. The fusion protein was constructed by recombinant techniques as described below.

Isolation of cDNA of Human IgG1 Heavy Chain Region and Construction of Plasmid pSAB144

In order to isolate a cDNA copy of the human IgG1 heavy chain region, RNA was prepared from COS7 cells which has been transiently transfected by the plasmid VCAM1-IgG1 (also known as pSAB133). Construction of plasmid VCAMI-IgG1 is described in PCT patent application WO 90/13300. The RNA was reverse transcribed to generate cDNA using reverse transcriptase and random hexamers as the primers. After 30 min. at 42° C., the reverse transcriptase reaction was terminated by incubation of the reaction at 95° C. for 5 min. The cDNA was then amplified by PCR (Polymerase Chain Reaction, see, e.g., Sambrook et al., *Molecular Cloning*, Vol. 3, pp. 14.1–14.35 (Cold Spring Harbor; 1989) [34]) using the following kinased primers: 370-31 (SEQ ID NO: 6 and SEQ ID NO: 13):

```
5'TCGTC GAC AAA ACT CAC ACA TGC C
      Asp Lys Thr His Thr Cys
``` which contains a SalI site, and 370-32 (SEQ ID NO: 7):
5'GTAAATGAGT GCGGCGGCCG CCAA, which encodes the carboxy terminal lysine of the IgG1 heavy chain constant region, followed by a NotI site.

The PCR amplified cDNA was purified by agarose gel electrophoresis and glass bead elution for cloning in plasmid pNN03. Plasmid pNN03 was constructed by removing the synthetic polylinker sequence from the commercially available plasmid pUC8 (Pharmacia, Piscataway, N.J.) by restriction endonuclease digestion and replacing the synthetic polylinker sequence with the following novel synthetic sequence (SEQ ID NO: 8): GCGGCCGCGG TCCAAC-CACC AATCTCAAAG CTTGGTACCC GGGAATTCAG ATCTGCAGCA TGCTCGAGCT CTAGATATCG ATTC-CATGGA TCCTCACATC CCAATCCGCG GCCGC.

The purified PCR amplified cDNA fragment was ligated to pNN03 which had been cleaved with EcoRV, dephosphorylated, and purified by low melt agarose gel electrophoresis. The ligation reaction was used to transform *E. coli* JA221 and the resulting colonies were screened for a plasmid containing an insert of approximately 700 bp. The identity of the correct insert was confirmed by DNA sequence analysis, and the plasmid was designated pSAB144.

Construction of Plasmid pSAB142

The plasmid pSAB1142 was constructed as follows. cDNA prepared from COS cells transfected with pSAB133 (as described in the previous section) was subjected to PCR amplification using oligonucleotides 370-01 and 370-29. Oligonucleotide 370-01 includes a NotI site and the nucleotides corresponding to amino acids 1 through 7 of the VCAM-1 signal sequence (SEQ ID NO: 9 and SEQ ID No: 14):

```
5' GAGCTCGAGG CGGCCGCACC ATG CCT GGG AAG ATG GTC
                            Met Pro Gly Lys Met Val
                                                GTG
                                                Val
```

Oligonucleotide 370–29 corresponds to the VCAM-1 amino acids 214-219 and includes a SalI site (SEQ ID NO: 10):
5'AA GTC GAC TTG CAA TTC TTT TAC The amplified DNA fragment was ligated to the vector fragment of pNN03, cleaved by EcoRV.

Construction of pSAB132 pJOD-S (Barsoum, J., *DNA and Cell Biol.*, 9, pp. 293–300 (1990) [35]) was modified to insert a unique NotI site downstream from the adenovirus major late promoter so that NotI fragments could be inserted into the expression vector. pJOD-S was linearized by NotI cleavage of the plasmid DNA. The protruding 5' termini were blunt-ended using Mung Bean nuclease, and the linearized DNA fragment was purified by low melting temperature agarose gel electrophoresis. The DNA fragment was religated using T4 DNA ligase. The ligated molecules were then transformed into *E. coli* JA221. Colonies were screened for the absence of a NotI site. The resulting vector was designated pJOD-S delta NotI. pJOD-8 delta NotI was linearized using SalI and the 5' termini were dephosphorylated using calf alkaline phosphatase. The linearized DNA fragment was purified by low melting temperature agarose gel electrophoresis and ligated in the presence of phosphorylated oligonucleotide ACE175, which has the following sequence (SEQ ID NO: 11): TCGACGCGGC CGCG The ligation mixture was transformed into *E. coli* JA221, and colonies were screened for the presence of a plasmid having a NotI site. The desired plasmid was named pMDR901.

In order to delete the two SV40 enhancer repeats in the Sv40 promoter which controls transcription of the DHFR cDNA, pMDR901 and pJODΔe-tPA (Barsoum, *DNA and Cell Biol.*, 9, pp. 293–300 (1990) [35]), both were cleaved with AatII and DraIII. The 2578 bp AatII-DraIII fragment from pMDR901 and the 5424 bp AatII-DraIII fragment from pJODΔe-tPA were isolated by low melting temperature agarose gel electrophoresis and ligated together. Following transformation into *E. coli* JA221, the resulting plasmid, pMDR902, was isolated. pSAB132 was then formed by eliminating the EcoRI-NotI fragment of pMDR902 containing the adenovirus major late promoter and replacing it with an 839 bp EcoRT-NotI fragment from plasmid pCMV-B (Clontech, Palo Alto, Calif.) containing the human cytomegalovirus immediate early promoter and enhancer.

Construction of pSAB146 pSAB144 was cleaved with SalI and NotI, and the 693 bp fragment isolated. pSAB142 was cleaved with NotI and SalI and the 664 bp fragment was isolated. The two fragments were ligated to pSAB132 which had been cleaved with NotI, and the 5' termini dephosphorylated by calf alkaline phosphatase. The resulting plasmid, pSAB146, contained the DNA sequence encoding the VCAM-1 signal sequence, the amino terminal 219 amino acids of mature VCAM-1, ten amino acids of the hinge region of IgG1 and the CH2 and CH3 constant domains of IgG1.

Production of VCAM 2D-IgG from a Stably

Transformed CHO Cell Line

A recombinant VCAM 2D-IgG expression vector was constructed as described below and transfected into CHO cells to produce a cell line continuously secreting VCAM 2D-IgG.

The 1.357 kb NotI fragment containing the VCAM 2D-IgG coding sequence of pSAB146 was purified by agarose gel electrophoresis. This fragment was ligated into the NotI cloning site of the expression vector pMDR901, which uses the adenovirus 2 major late promoter for heterologous gene expression and the selectable, amplifiable dihydrofolate reductase (dhfr) marker. The ligated DNA was used to transform *E. coli* DH5. Colonies containing the plasmid with the desired, correctly oriented insert were identified by the presence of 5853 and 3734 bp fragments upon digestion with Hind III; and 4301, 2555, 2293, and 438 bp fragments upon digestion with Bg III. The resultant recombinant VCAM 2D-IgG expression vector was designated pEAG100. The identity of the correct insert was confirmed by DNA sequence analysis.

The recombinant expression plasmid pEAG100 was electroporated into dhfr-deficient CHO cells according to the published protocol of J. Barsoum (DNA Cell Biol 9: 293–300, 1990 [35]), with the following changes: 200 µg of PvuI-linearized pEAG100 plasmid and 200 µg of sonicated salmon sperm DNA were used in the electroporation protocol. In addition, cells were selected in alpha-complete medium supplemented with 200 nM methotrexate.

To determine expression levels of secreted VCAM 2D-IgG, clones were transferred to a flat bottom 96 well microtiter plate, grown to confluency and assayed by ELISA as described below.

Wells of Immunol 2 plates (Dynatech, Chantilly, Va.) were each coated with anti-VCAM MAb 4B9 (isolated and purified on Protein A Sepharose as described by Carlos et al, 1990 [56]) with 100 µl of anti-VCAM 4B9 MAb diluted to 10 µg/ml in 0.05 M sodium carbonatelbicarbonate buffer, pH 9.6, covered with Parafilm, and incubated overnight at 4° C. The next day, the plate contents were dumped out and blocked with 200 µl/well of a block buffer (5% fetal calf serum in 1×PBS), which had been filtered through a 2 filter. The buffer was removed after a 1 hour incubation at room temperature and the plates were washed twice with a solution of 0.05% Tween-20 in 1×PBS. Conditioned medium was added at various dilutions. As a positive control, an anti-mouse Ig was also included. Block buffer and LFA-3TIP constituted as negative controls. The samples and controls were incubated at room temperature for 2 hours.

The plates were then washed twice with a solution of 0.05% Tween-20 in 1×PBS. Each well, except for the positive control well, was then filled with 50 µl of a 1:2000 dilution of HRP-Donkey anti-human IgG (H+L) (Jackson Immulon Research Laboratories, Inc.; West Grove, Pa.) in block buffer. The positive control well was filled with 50 µl of a 1:2000 dilution of HRP-Goat anti-mouse IgG (H+L) (Jackson Immune Research Laboratories, Inc.; West Grove, Pa.) in block buffer. The plates were then incubated for 1 hour at room temperature.

The HRP conjugated Ab solutions were removed, and the wells were washed twice with 0.05% Tween-20 in 1×PBS. Then, 100 µl of HRP-substrate buffer was added to each well at room temperature. HRP-substrate buffer was prepared as follows: 0.5 ml of 42 mM 3,3',5,5'-tetramethylbenzidine (TMB), (ICN Immunobiologicals, Lisle, S.C., Catalogue No. 980501) in DMSO (Aldrich) was slowly added to 50 ml of substrate buffer (0.1 M sodium acetate/citric acid, pH 4.9); followed by addition of 7.5 µl of 30% hydrogen peroxide (Sigma, Catalogue No. H-1009).

The development of a blue color in each well was monitored at 650 nm on a microtiter plate reader. After 7–10 minutes, the development was stopped by the addition of 100 µl of 2N Sulfuric acid. The resulting yellow color was read at 450 mn on a microtiter plate reader. A negative control well was used to blank the machine.

Purification of VCAM 2D-IgG

CHO cells expressing VCAM 2D-IgG were grown in roller bottles on collagen beads. Conditioned medium (5 Liters) was concentrated to 500 ml using an Amicon S1Y10 spiral ultrafiltration cartridge (Amicon, Danvers, Mass.). The concentrate was diluted with 1 liter of Pierce Protein A binding buffer (Pierce, Rockford, Ill.) and gravity loaded onto a 10 ml Protein A column (Sepharose 4 Fast Flow, Pharmacia, Piscataway, N.J.). The column was washed 9 times with 10 ml of Protein A binding buffer and then 7 times with 10 ml of PBS. VCAM 2D-IgG was eluted with twelve-5 ml steps containing 25 mM $H_3PO_4$ pH 2.8, 100 mM NaCl. The eluted samples were neutralized by adding 0.5 M $Na_2HPO_4$ pH 8.6 to 25 mM. Fractions were analyzed for absorbance at 280 nm and by SDS-PAGE. The three peaks fractions of highest purity were pooled, filtered, aliquoted and stored at −70° C. By SDS-PAGE, the product was greater than 95% pure. The material contained less than 1 endotoxin unit per mg of protein. In some instances, it was necessary to further purify the Protein A eluate product on Q-Sepharose FF (Pharmacia). The protein A eluate was diluted with 3 volumes of 25 mM Tris HCl pH 8.0 and loaded onto a Q-Sepharose FF column at 10 mg VCAM 2D-IgG per ml of resin. The VCAM 2D-IgG was then eluted from the Q-Sepharose with PBS.

Evaluation of VCAM 2D-IgG

The following examples (Example VI–VIII) have been included to provide evidence that the VCAM-Ig parallels the efficacy of anti-α4 monoclonal antibodies in vivo in three out of three models studied below. Two murine models, contact hypersensitivity model and NOD diabetic mouse model have been tested with the VCAM-Ig fusion protein, as well as the sheep asthma model. The sheep asthma model is quite distinct from the mouse models in that: 1) it is a different species; 2) a different organ (lung, versus skin or pancreas); 3) the leukocytes targeted are unknown (i.e. not clearly T cell dependent classical immune reaction); 4) aerosol versus i.v./i.p. administration; 5) mAbs used are different (anti-murine-α4 mAbs PS/2 and R1/2 in mice versus anti-human-α4 mAb HP1/2 in sheep). Therefore, using the correlation between VCAM-Ig and the anti-α4 mAbs provided by the examples below, strong evidence has been generated that the VCAM-Ig fusion protein would be effective in the treatment of IBD because the anti-human-α4 mAb HP1/2 has been proven effective in the cotton top tamarin trials described above.

EXAMPLE VI

The Effect of VCAM-Ig on the Murine Contact Hypersensitivity Response

The experiments described below can be performed essentially as follows.

BALB/c mice (purchased from Taconic Farms, Germantown, N.Y.) were sensitized to 2,4-Dinitrofluorobenzene (DNFB)(Aldrich Chemical Co., Wis.) by the application of 25 µg of 0.5% DNFB in an acetone/olive oil vehicle (4:1 v/v) on day 0 and again on day 1 to the shaved abdominal skin (see, *Current Protocols in Immunology*, John Wiley and Sons, NY 1001, Section 4.2). Mice were sensitized to oxazalone by the application of 150 µl of 3.0% oxazalone in 100% ethanol to the shaved abdominal skin on day 0 (see, *Current Protocols in Immunology*, John Wiley and Sons, NY 1001, Section 4.2). For the day 0 sensitization procedure the mice were lightly anesthetized with avertin (0.010–0.015 ml/h body weight of 2.5% avertin stock, intraperitoneal). Immediately prior to challenge, baseline ear thickness measurements were recorded in units of $10^{-4}$ inches, for both ears of all of the mice, using a Mitutoyo engineer's micrometer (see, *Current Protocols in Immunology*, John Wiley and Sons, NY 1001, Section 4.2). All measurements were done in quadruplicate and summarized as mean thickness±SEM. The DNFB response was elicited on day 5 by skin-painting the dorsal surface of the left ear with 10 µl of 0.2% DNFB in 4:1 acetone/olive oil. The dorsal surface of the right (control) ear was painted with 10 µl of vehicle only and was a specificity control for the reaction. The oxazalone response was elicited on day 6 by painting the dorsal surface of the left ear with 20 µl of 1% oxazalone in ethanol. The right ear was painted with 20 µl of ethanol. The CHS response was assessed by obtaining 24-h ear thickness measurements. The average change in left ear thickness (ΔT) for each group was determined by substituting baseline ear thickness from 24-h ear thickness. The immunomodulatory effect of the antibody treatment was evaluated by calculating the percentage inhibition as follows: % Inhibition=[1-ΔT treatment/ΔT control]×100%.

Figure 2:
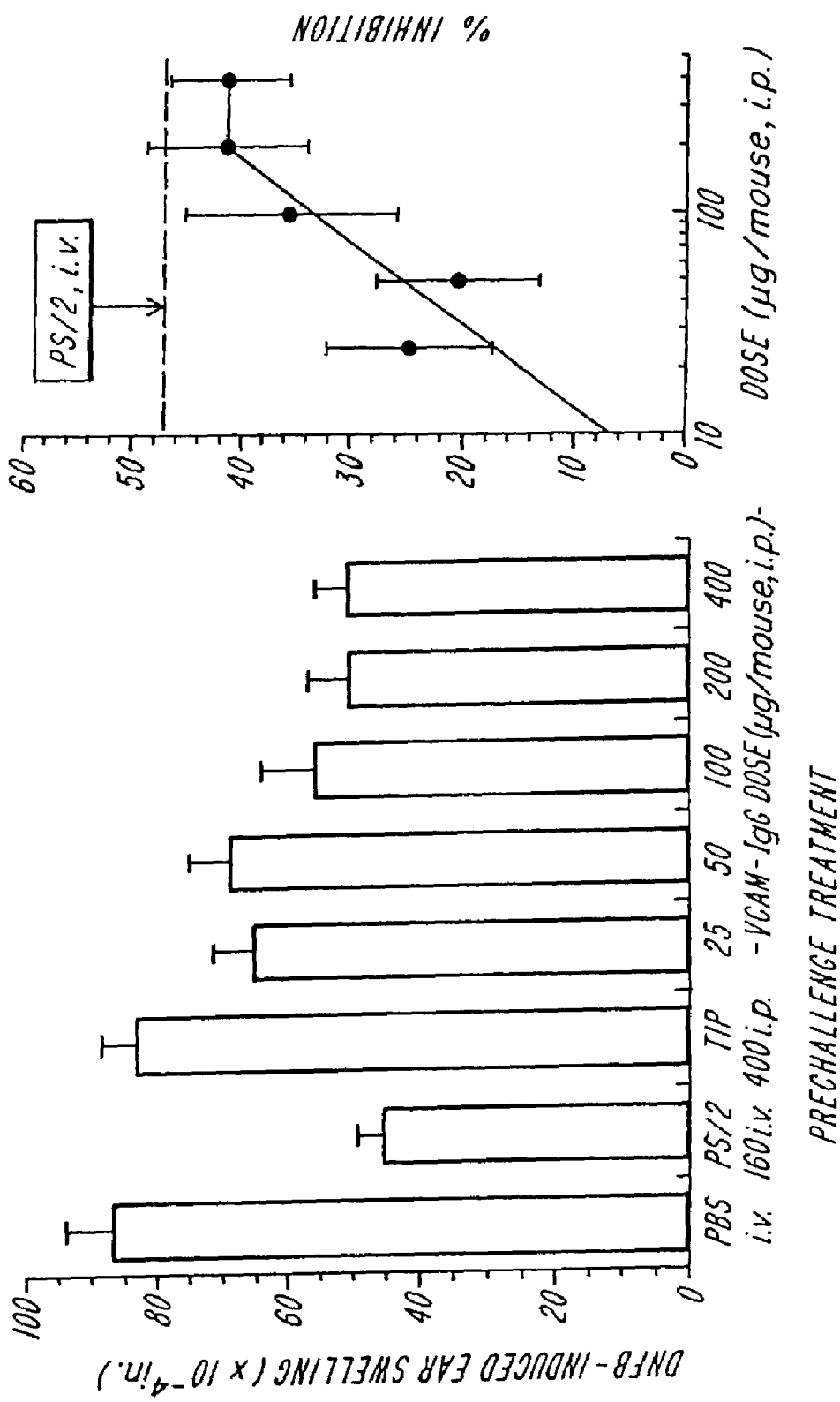

VCAM-IgG was administered to mice in varying intraperitoneal doses, 4–6 hours prior to challenge. VCAM-IgG was administered in pyrogen-free, azide-free PBS. As shown in FIG. 2, VCAM-IgG tested over a dose range of 1.25 to 20 mg/kg (25–400 µg/mouse) maximally inhibited the mouse ear swelling response about 4/5 as well as the PS/2 antibody, which is a IgG2b rat anti-mouse α-4 antibody (anti-VLA4 antibody). Maximal inhibition was observed at the 10 mg/kg dose. The ED50 was about 2.5 mg/kg, i.p. (50 µg/mouse).

Figure 3:
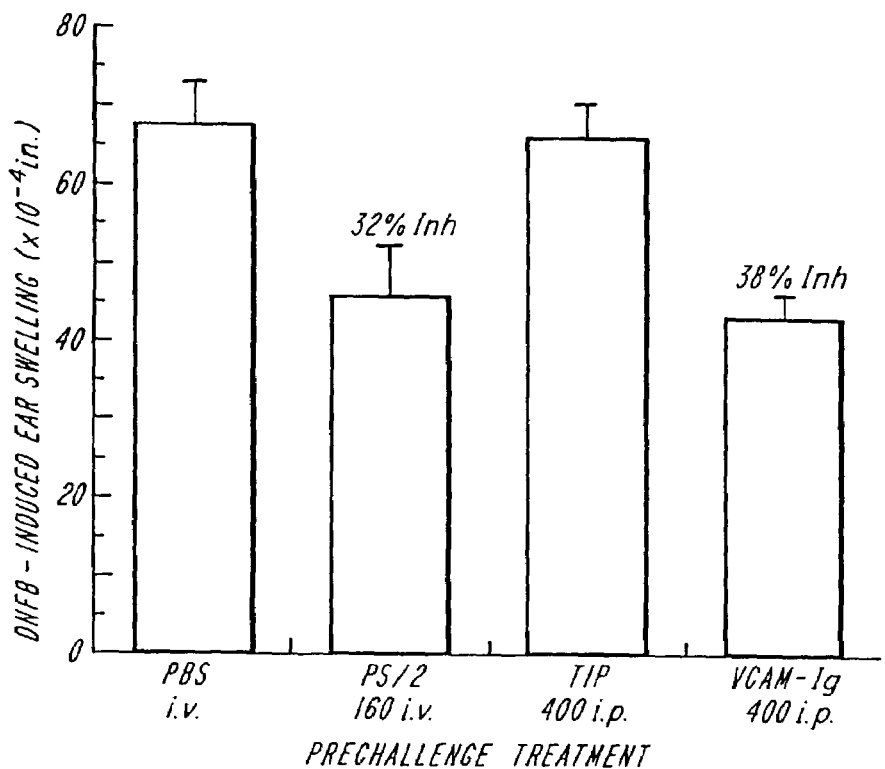

In a confirmation study (FIG. 3), VCAM-IgG tested at 20 mg/kg i.p. (400 µg/mouse) maximally inhibited the mouse ear swelling response as effectively as the PS/2 8 mg/kg i.v. antibody dose.

In summary, VCAM-IgG at optimal dose can block the skin CHR response by about 40–50%, just as well as does an optimal dose of the PS/2 antibody.

EXAMPLE VII

The Effect of VCAM-IG Treatment on Adoptive Transfer of Diabetes

For the adoptive transfer of diabetes experiments, NOD mice were obtained from Taconic Farms (Germantown, N.Y.) or from the Joslin Diabetes Center (Boston, Mass.). Spontaneously diabetic (D) females of recent onset (13–20 weeks of age) were used as spleen cell donors and 8 week old nondiabetic (Y) females served as recipients. Spleen cells from 4 week old nondiabetic (Y) female donors which fail to transfer disease were used as a negative control.

Recipient mice were placed on acidified water (1:8400 dilution of concentrated HCl in water) one week prior to sublethal irradiation (775 rad) performed in split doses (300 rad, 300 rad, and 175 rad) on each of three days (day −2, −1, and the day of transfer), in order to minimize any incidence of intestinal infection subsequent to high dose irradiation (Gamma Cell 1000 Cesium $^{137}$ source, Nordion International, Inc., Ontario, Canada). Spleens were harvested from diabetic donors or from nondiabetic controls, cell suspensions made and red cells lysed with Hemolytic Geys solution. Spleen cells were injected intravenously ($2–3\times10^7$ in 0.2 ml PBS) and were pretreated with either 100 µg VCAM 2D-IgG or 100 µg of irrelevant LFA-3Ig fusion protein control. Another group received PBS alone without cells transferred. The fusion protein LFA-3Ig (LFA-3TIP) was isolated and purified as described in PCT US92/02050 and Miller et al., 1993 [36]. The VCAM 2D-IgG fusion protein or irrelevant LFA-3Ig protein was administered at a dose of 100 µg/0.2 ml intraperitoneally twice weekly through day 17. This concentration was sufficient to provide a serum level of fusion protein sufficient to saturate VLA4-positive cells, the serum levels determined by ELISA as described above. Diabetes onset was monitored as described above.

Figure 4:
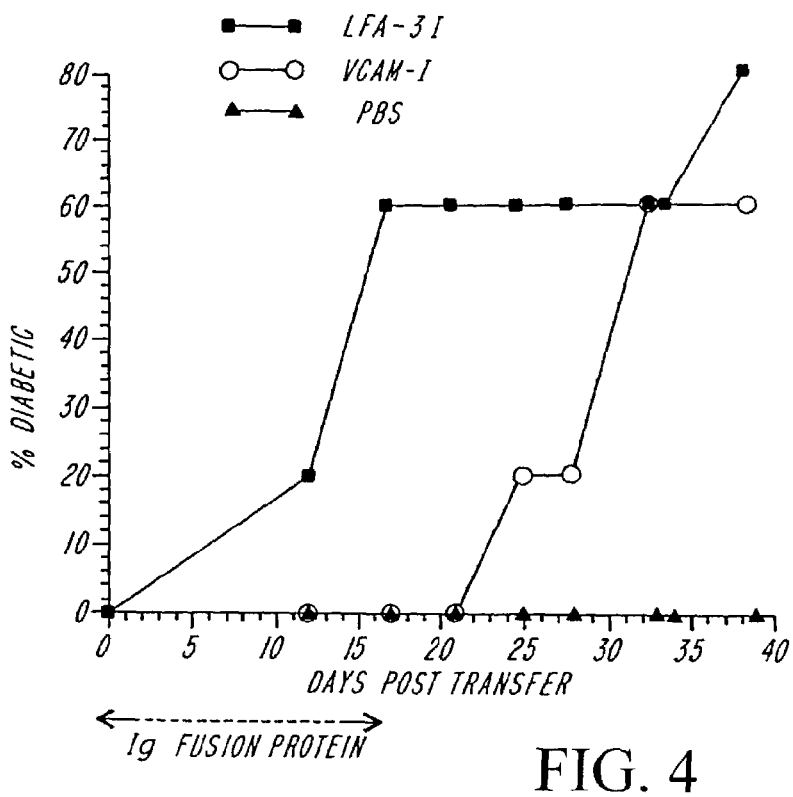

The results of the evaluation are shown in FIG. 4. As shown in this Figure, VCAM 2D-IgG fusion protein significantly inhibits the onset of diabetes in recipients of cells from diabetic donor mice (DNVCAM-Ig, open circles) with 60% incidence by day 30 post-transfer, as compared to the mice which received cells from diabetic donor (data not shown) and LFA-3Ig irrelevant control Ig fusion protein (D/LFA-3 Ig) which had already achieved 60% incidence by day 15 post-transfer. Mice which received no cells (PBS only) did not develop disease. There were n=5 mice per experimental group.

EXAMPLE VIII

The Effect of VCAM-IG Treatment on the Sheep Model of Airways Hyper-Responsiveness Experiments were performed essentially as described by Abraham et al. [33]. Briefly, allergic sheep having natural allergic cutaneous reaction to 1:1000 or 1:10,000 dilutions of *Ascaris suum* extract (Greer Diagnostics, Lenoir N.C.) were tested, and sheep demonstrating both early and late phase airway response ("dual responders") to inhalation challenge with *Ascaris suum* antigen were selected. To measure breathing mechanics and physical changes in the airways, the sheep were restrained in a prone position with heads immobilized. A balloon catheter was advanced through one nostril under topical anesthesia with 2% lidocaine solution to the lower esophagus, and a cuffed endotracheal tube was advanced through the other nostril (using a flexible fiberoptic bronchoscope as a guide) for the measurement of airway mechanics and during aerosol challenges. Pleural pressure was estimated with the esophageal balloon catheter (filled with 1 ml of air) positioned 5–10 cm from the gastroesophageal junction. In this position, end expiratory pleural pressure ranged between −2 and −5 cm $H_2O$. Once the balloon was placed, it was secured so that it remained in position for the duration of the experiment. Lateral pressure in the trachea was measured with a sidehole catheter, (inner diam. 2.5 mm) advanced through and positioned distal to the tip of the endotracheal tube. Transpulmonary pressure (the difference between tracheal and pleural pressure) was measured with a differential pressure transducer catheter system (MP45, Validyne, Northridge, Calif.). The pressure transducer catheter system showed no phase shift between pressure and flow to a frequency of 9 $H_z$. Pulmonary resistance ($R_L$) was measured by connecting the proximal end of the endotracheal tube to a Fleich pneumotachograph (Dyna Sciences, Blue Bell Pa.). Signals indicating flow and transpulmonary pressure were recorded on an oscilloscope recorder (Model DR-12; Electronics for Medicine, White Plains, N.Y.) linked to a computer for automatic calculation of pulmonary resistance ($R_L$) from transpulmonary pressure, respiratory volume (obtained by digital integration) and flow by the mid-volume technique, analyzed from 5–10 breaths. Thoracic gas volume ($V_{tg}$) was measured immediately after determination of $R_L$ in a constant volume body plethysmograph. Specific lung resistance ($SR_L$) was calculated from these values ($SR_L=V_{tg} \times R_L$).

Airway responsiveness was determined by performing dose response curves to inhaled carbachol. The dose response curves were plotted using measurements of $SR_L$ taken immediately after inhalation of buffer (PBS) alone and after each consecutive administration of 10 breaths of increasing concentrations of carbachol in PBS. The concentrations of carbachol were 0.25%, 0.5%, 1.0%, 2.0% and 4.0% wt/vol in PBS. The provocation test was discontinued when $SR_L$ increased over 400% from the post-PBS value or after the highest carbachol concentration had been administered. Airway responsiveness was determined by calculating from the dose response curves the cumulative carbachol dose in breath units (BU) that increased specific lung resistance 400% over the post buffer value ($PD_{400\%}$). One breath unit was defined as one breath of a 1% wt/vol carbachol solution. Thus, the greater the suppression of airway hyper-responsiveness, the greater the number of breath units would be required before observing the same bronchoconstriction as seen in the controls.

Each sheep was subjected to a trial as a control in which a placebo (PBS without additive) was used as a pretreatment 30 minutes before allergen challenge with *Ascaris suum* antigen (Greer Diagnostics, Lenoir, N.C.). The antigen solution was delivered as an aerosol using a disposable medical nebulizer (RAINDROP®, Puritan Bennett, Lenexa, Kans.) that provided an aerosol with a mass median aerodynamic diameter of 3.2 μM (geometric SD 1.9) as determined by an Andersen cascade impactor. The *Ascaris suum* extract was diluted in PBS to a concentration of 82,000 Protein Nitrogen Units(PNU)/ml. The output of the nebulizer was directed into a plastic T-tube, one end of which was connected to the inspiratory port of a Harvard respirator. A dosimeter connected to the nebulizer consisting of a solenoid valve and a 20 psi compressed air source and the solenoid valve was activated at the beginning of the inspiratory cycle of the Harvard respirator for one second. The aerosol delivered at a tidal volume of 500 ml and a rate of 20 breaths per min. for 20 min. Each sheep was challenged with an equivalent dose of antigen (400 breaths) in the control and VCAM1-IgG1 trials. Carbachol aerosols for the dose response curves were also generated by nebulizer as described above.

An airway challenge trial using five pairs of responder allergic sheep was conducted in order to investigate the efficacy of VCAM1-IgG1 (VCAM-Ig) fusion protein in the sheep model of airways hyper-responsiveness. The efficacy of the aerosol delivery of the VCAM-Ig was investigated. VCAM-Ig was delivered via nebulizer in the form of an aerosol.

Figure 5:
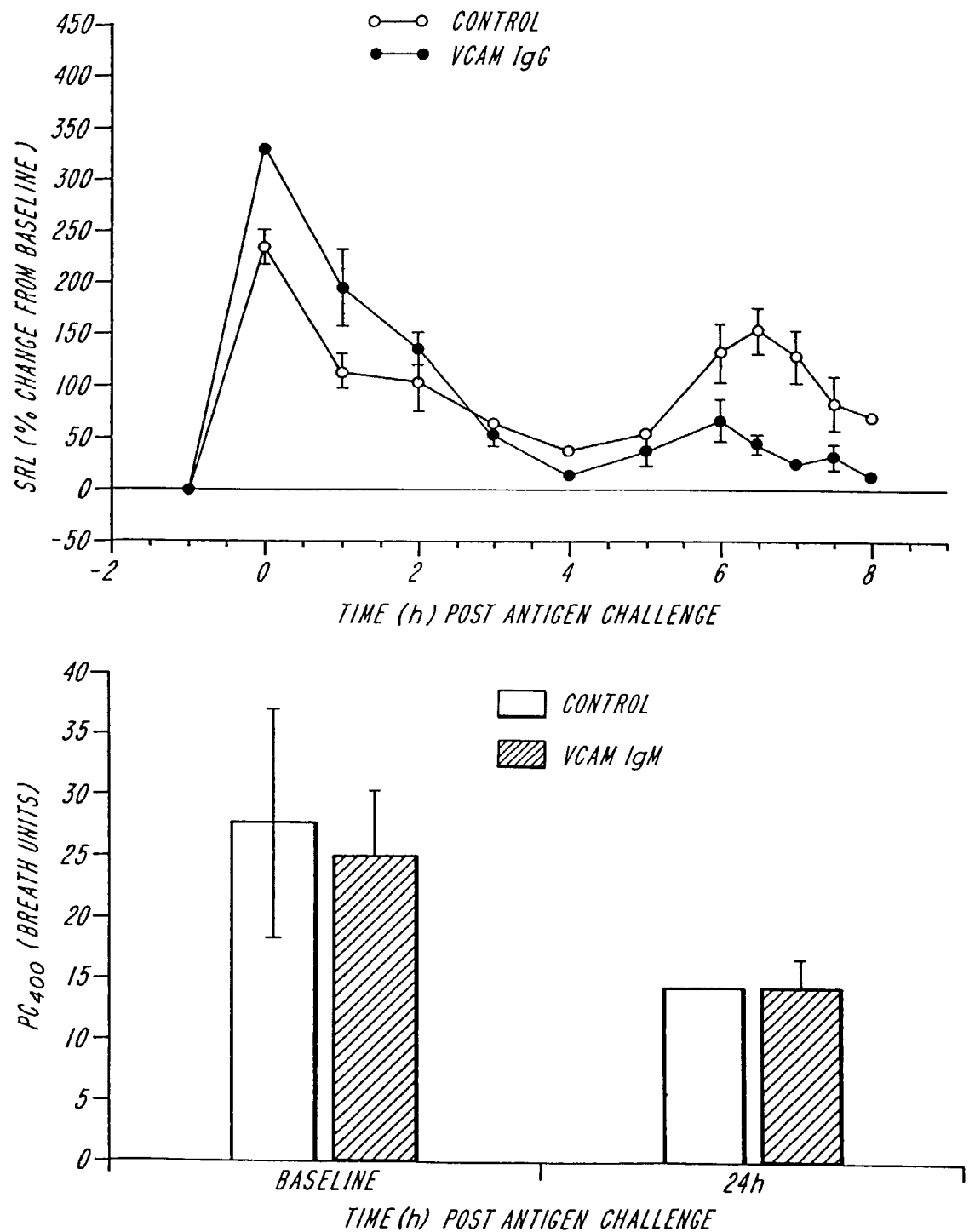
FIG. 5 is a graph depicting the effect of VCAM-Ig (30 mg, aerosol given 30 min before antigen challenge) on airway hyperresponsiveness in dual responder sheep. This dose resulted in significant but partial inhibition of LPR, but no effect on AHR.
Figure 6:
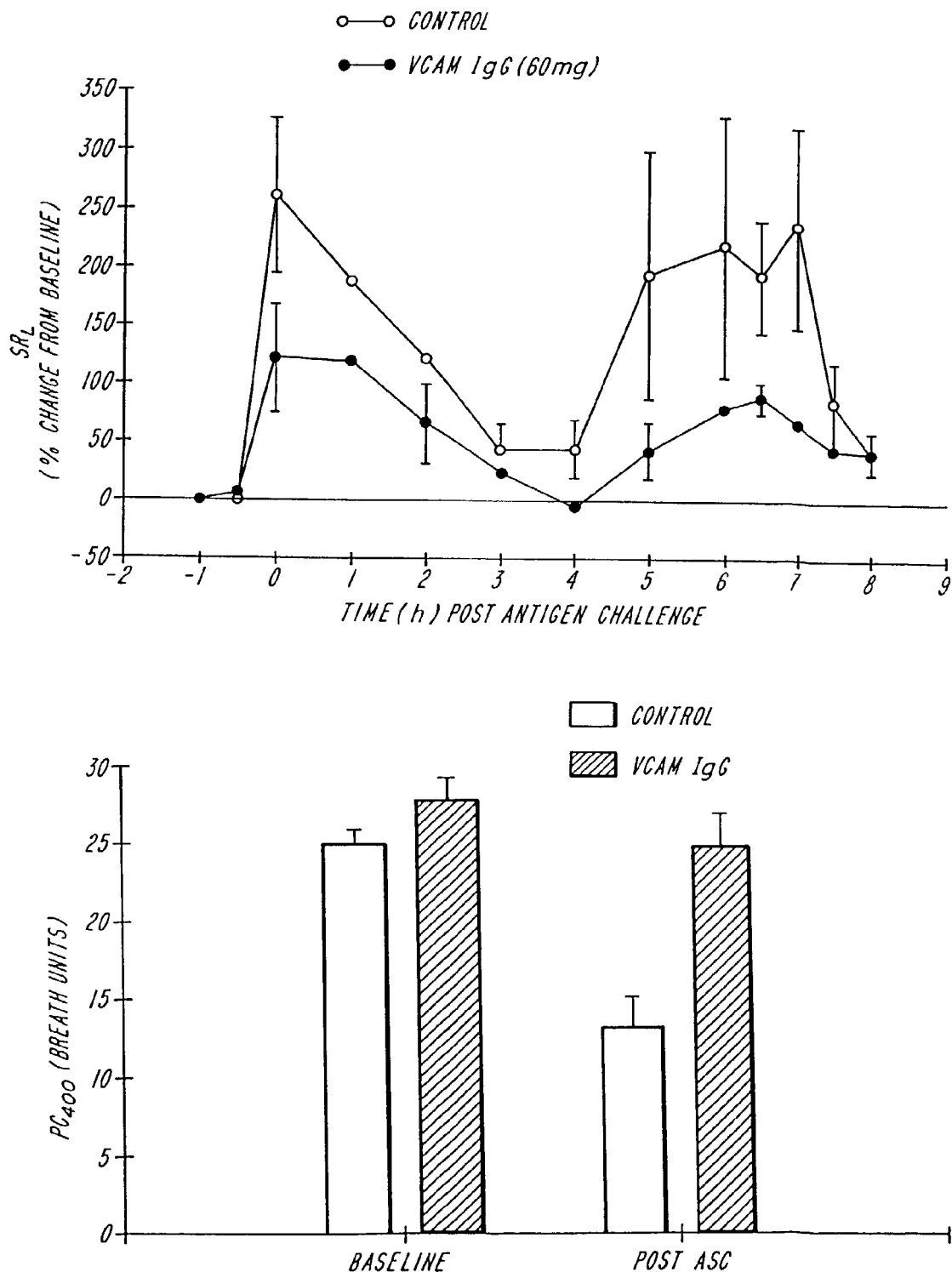
FIG. 6 is a graph depicting the effect of VCAM-Ig (60 mg, aerosol given 30 min before antigen challenge) on airway hyperresponsiveness in dual responder sheep. This dose resulted in significant but partial inhibition of LPR, and inhibition of AHR.
Figure 7:
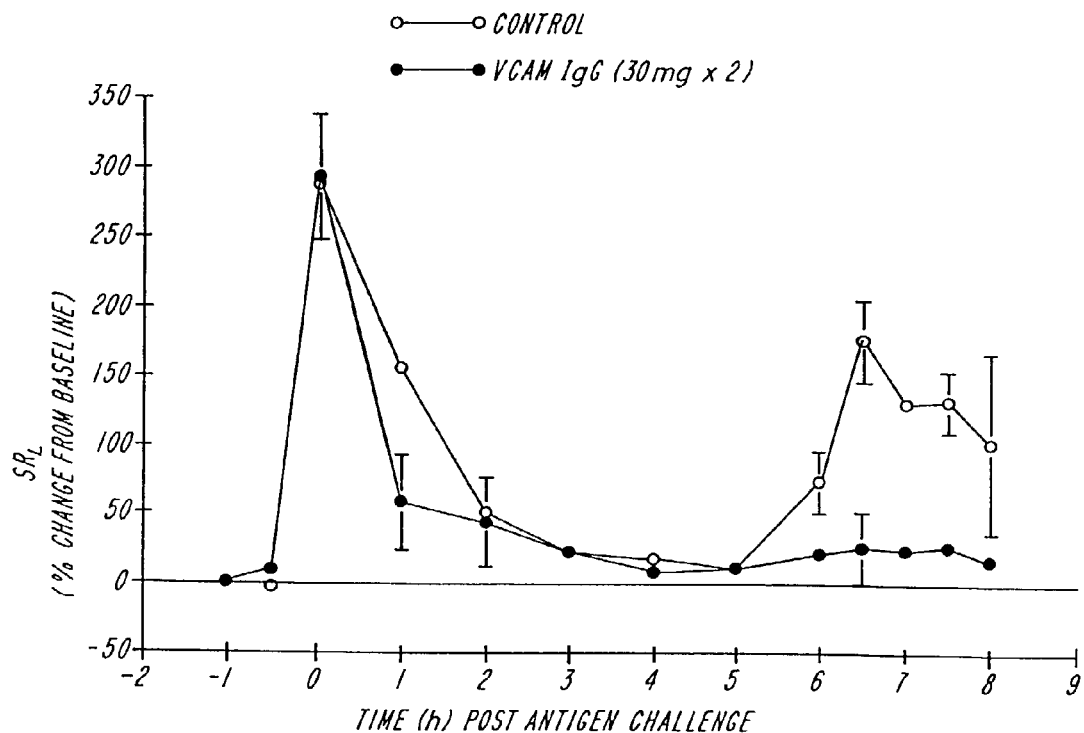
FIG. 7 is a graph depicting the effect of VCAM-Ig (30 mgs, aerosol given 30 min. before antigen challenge and 8 h. after challenge) on airway hyperresponsiveness in dual responder sheep. This dose resulted in complete inhibition of LPR, but no inhibition of AHR.
Figure 7:
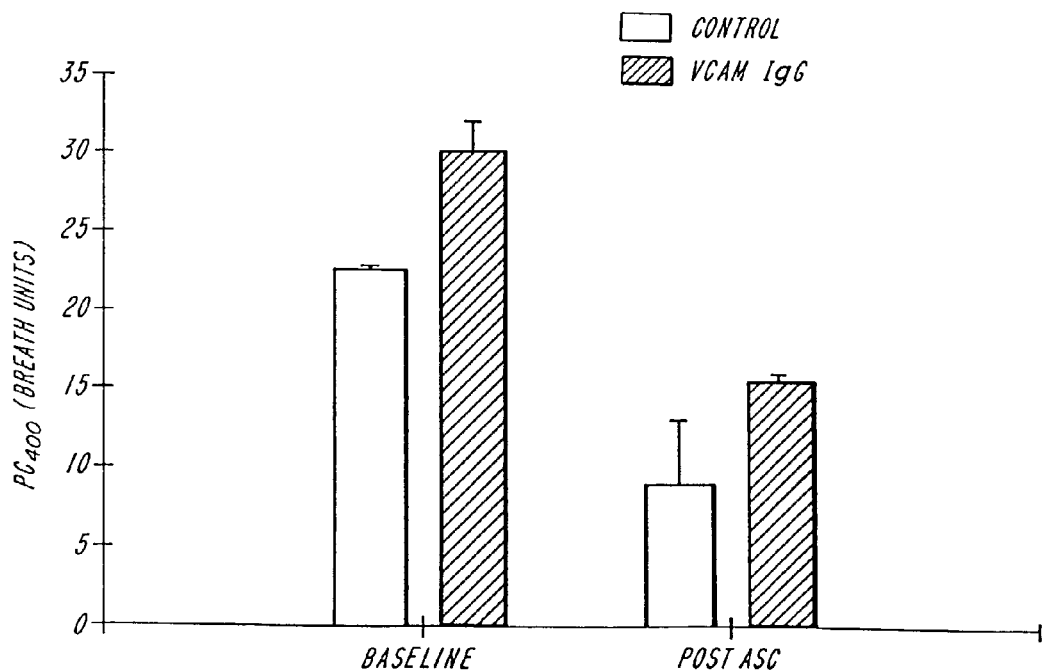
Figure 8:
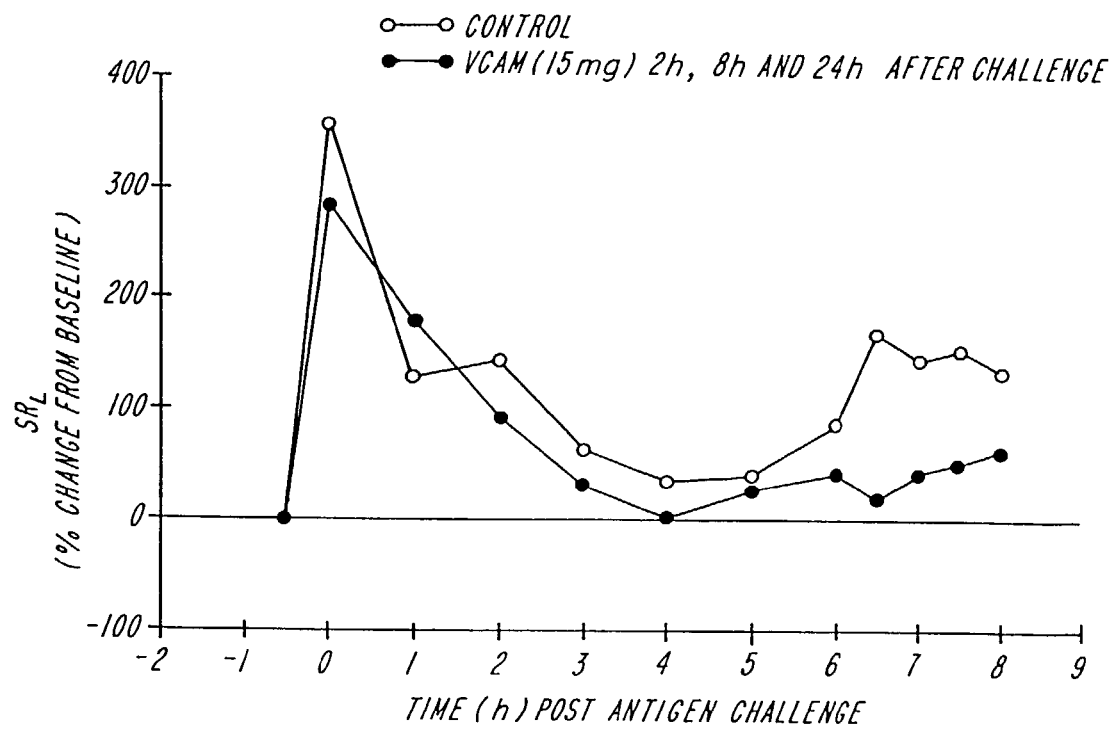
FIG. 8 is a graph depicting the effect of VCAM-Ig (15 mgs, aerosol given 2, 8 and 24 h. after antigen challenge) on airway hyperresponsiveness in dual responder sheep. This dose resulted in a significant but partial inhibition of LPR, and inhibition of AHR.
Figure 8:
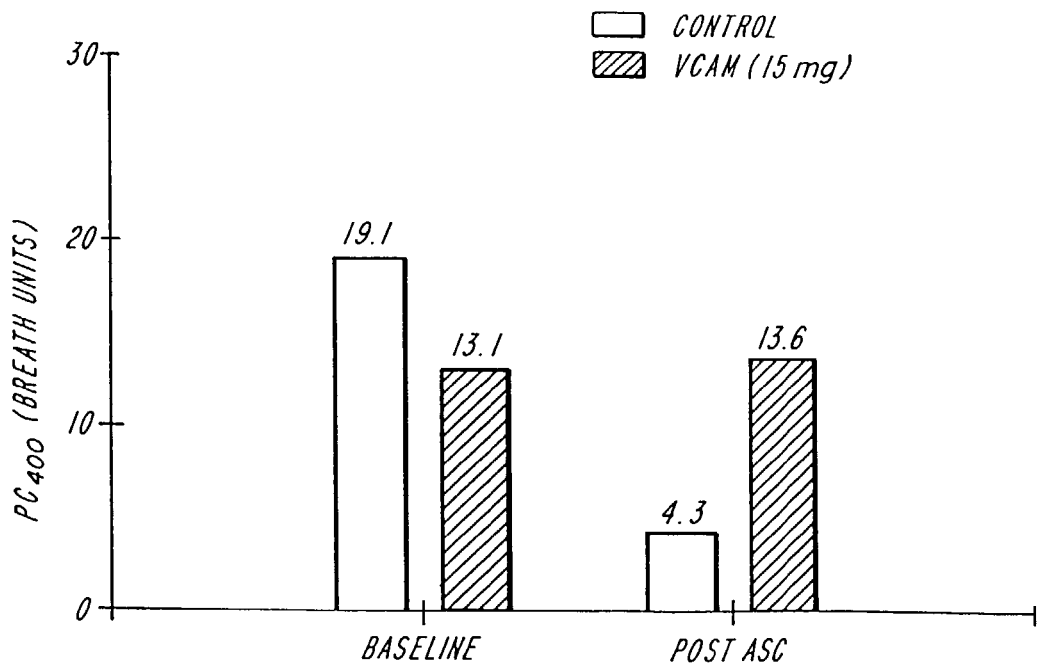
Figure 9:
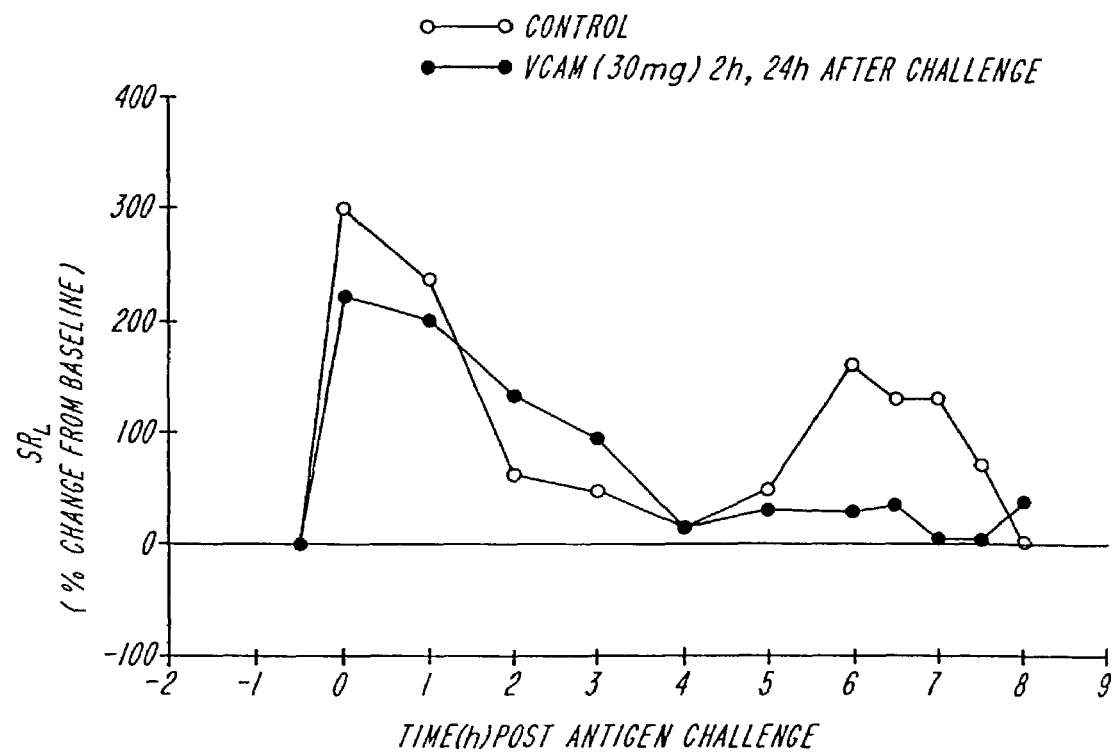
FIG. 9 is a graph depicting the effect of VCAM-Ig (30 mgs, aerosol given 2, and 24 h. after antigen challenge) on airway hyperresponsiveness in dual responder sheep. This optimal dose resulted in complete inhibition of both LPR and AHR.
Figure 9:
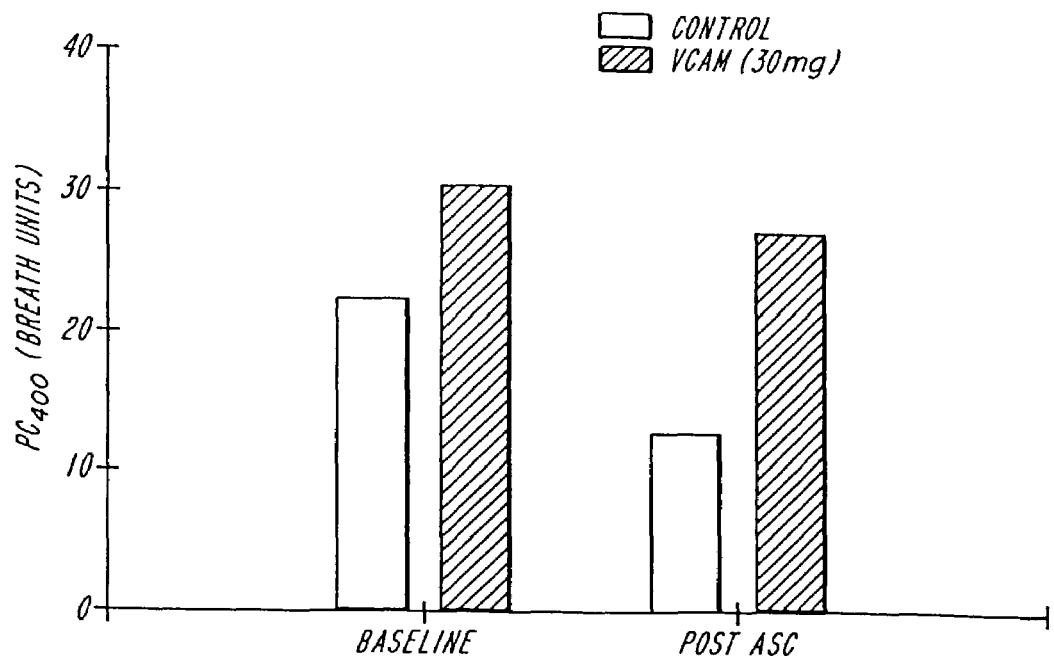

In order to optimize therapeutic efficacy, aerosolized VCAM-Ig was first administered at different dosing regimens. These experiments are summarized in FIGS. 5–9. In all the experiments, the control sheep received placebo. In the first experiment, two animals were given 30 mg VCAM-Ig (1 mg/kg) at 30 minutes prior to antigen challenge, which is the standard time used for other therapeutic agents. Under these conditions significant but partial inhibition of the late phase response (LPR) but no effect on airways hyper-responsiveness (AHR) was observed (FIG. 5). This result was not surprising as VCAM-Ig was found previously to be a little less potent than mAb HP1/2. In the second experiment, therefore, the dose of VCAM-Ig was increased to 60 mg. This dose resulted in the partial blockage of LPR as in the previous experiment, but now AHR was blocked too (FIG. 6). However, due to the serious problems which resulted from attempting to aerosolize such a large volume, in subsequent experiments dosages were administered at different time intervals. In the third experiment, 30 mg of VCAM-Ig were administered at 30 minutes prior to and 8 hours after antigen challenge. Here the LPR was blocked completely but no blockage of the AHR was observed (FIG. 7). With respect to the LPR this represented a single dose 30 minutes prior to antigen challenge (equivalent to experiment 1) because the second dose at 8 hours was given after the LPR was largely over. In the fourth experiment, 15 mg of VCAM-Ig were administered at 2, 8 and 24 hours. Here partial blockage of the LPR and blockage of the AHR was observed (FIG. 8). In the final experiment, 30 mg of VCAM-Ig were administered at 2 and 24 hours and resulted in complete blockage of both the LPR and AHR (FIG. 9). This optimal dosage was tested on four animals with the same result.

In summary, ten animals have all shown partial or complete inhibition of the LPR versus a placebo control, and complete inhibition of both the LPR and AHR can be achieved under optimal conditions (30 mg of VCAM-Ig administered at 2 and 24 hours after antigen challenge).

The foregoing examples are intended as an illustration of the method of the present invention and are not presented as a limitation of the invention as claimed hereinafter. From the foregoing disclosure, numerous modifications and additional embodiments of the invention will be apparent to those experienced in this art. For example, actual dosage used, the type of antibody, antibody fragment or analog used, mode of administration, exact composition, time and manner of administration of the treatment, and many other features all may be varied without departing from the above description. All such modifications and additional embodiments are within the contemplation of this application and within the scope of the appended claims.

CITED PUBLICATIONS

[1] D. Podolsky, "Colonic Glycoproteins in Ulcerative Colitis: Potential Meaning in Heterogeneity, *"Inflammatory Bowel Diseases: Basic Research and Clinical Implications*, Falk Symposium, Titisee, Germany, Jun. 7–9, 1987 (Kluwer Academic Publishers; Boston 1987) pp. 449–56.

[2] D. Podolsky and D. Fournier, "Alterations in Mucosal Content of Colonic Glycoconjugates in Inflammatory Bowel Disease Defined by Monoclonal Antibodies, *Gastroenterology*, 95, pp. 379–87 (1988).

[3] D. Podolsky and D. Fournier, "Emergence of Antigenic Glycoprotein Structures in Ulcerative Colitis Detected Through Monoclonal Antibodies," *Gastroenterology*, 95, pp. 371–8 (1988).

[4] G. Malizia et al., "Expression of Leukocyte Adhesion Molecules by Mucosal Mononuclear Phagocytes in Inflammatory Bowel Disease," *Gastroenterology*, 100, pp. 150–9 (1991).

[5] T. Springer, "Adhesion Receptors of the Immune System," *Nature*, 346, pp. 425–34 (August 1990).

[6] A. Freedman et al., "Adhesion of Human B Cells to Germinal Centers In Vitro Involves VLA-4 and INCAM-110," *Science*, 249, pp. 1030–33 (1990).

[7] G. E. Rice et al., "Vascular and Nonvascular Expression of INCAM-110, *Amer. J. Pathology*, 138(2), pp. 385–93 (1991).

[8] L. Burkly, et al., "Signaling by Vascular Cell Adhesion Molecule-1 (VCAM-1) Through VLA-4 Promotes CD3-dependent T Cell Proliferation," *Eur. J. Immunol.*, 21, pp. 2871–75 (1991).

[9] N. Damle and A. Aruffo, "Vascular Cell Adhesion Molecule 1 Induces T-cell Antigen Receptor-dependent Activation of CD4$^+$ T Lymphocytes," *Proc. Natl. Acad. Sci. USA*, 88, pp. 6403–7 (1991).

[10] G. van Seventer et al., "Analysis of T Cell Stimulation by Superantigen Plus Major Histocompatibility Complex Class II Molecules or by CD3 Monoclonal Antibody: Costimulation by Purified Adhesion Ligands VCAM-1, ICAM-1, but Not ELAM-1," *J. Exp. Medicine*, 174, pp. 901–13 (1991).

[11] Kohler and Milstein, "Continuous Cultures of Fused Cells Secreting Antibody of Predefined Specificity," *Nature*, 256, pp. 495–7 (1975).

[12] F. Sanchez-Madrid et al., "VLA-3: A novel polypeptide association within the VLA molecular complex: cell distribution and biochemical characterization," *Eur. J. Immunol.*, 16, pp. 1343–9 (1986).

[13] M. E. Hemler et al., "Characterization of the Cell Surface Heterodimer VLA-4 and Related Peptides," *J. Biol. Chem.*, 262(24), pp. 11478–85 (1987).

[14] M. Elices et al., "VCAM-1 on Activated Endothelium Interacts with the Leukocyte Integrin VLA-4 at a Site Distinct from the VLA-4/Fibronectin Binding Site," *Cell*, 60, pp. 577–84 (1990).

[15] R. Pulido et al., "Functional Evidence for Three Distinct and Independently Inhibitable Adhesion Activities Mediated by the Human Integrin VLA-4," *J. Biol. Chem.*, 266(16), pp. 10241–5 (1991).

[16] D. Podolsky, et al., "Colonic Mucin Composition in Primates Selective Alterations Associated with Spontaneous Colitis in the Cotton-top Tamarin," *Gastroenterology*, 88, pp. 20–5 (1985).

[17] D.-Podolsky et al., "Spontaneous Colitis In Cotton-Top Tamarins: Histologic, Clinical and Biochemical Features of an Animal Model of Chronic Colitis," *Digestive Diseases and Sciences*, 30(4), Abstract, p. 396 (1985).

[18] J. Madara et al., "Characterization of Spontaneous Colitis in Cotton-Top Tamarin (*Saguinus oedipus*) and Its Response to Sulfasalazine," *Gastroenterology*, 88, pp. 13–19 (1985).

[19] P. Jones et al., "Replacing the Complementarity-Determining Regions in a Human Antibody with Those From a Mouse," *Nature*, 321, pp. 522–25 (1986).

[20] E. Ward et al., "Binding Activities of a Repertoire of Single Immunoglobulin Variable Domains Secreted From *Escherichia coli,"* *Nature*, 341, pp. 544–6 (1989).

[21] U.S. Pat. No. 4,816,397, Boss et al., "Multichain Polypeptides or Proteins And Processes For Their Production", issued Mar. 28, 1989.

[22] L. Riechmann et al., "Reshaping Human Antibodies for Therapy," *Nature*, 332, pp. 323–7 (1988).

[23] Man Sun Co et al., "Humanized Antibodies for Antiviral Therapy," *Proc. Natl. Acad. Sci. USA*, 88, pp. 2869–73 (1990).

[24] P. Brown, Jr. et al., "Anti-Tac-H, a Humanized Antibody to the Interleukin 2 Receptor, Prolongs Primate Cardiac Allograft Survival," *Proc. Natl. Acad. Sci. USA*, 88, pp. 2663–7 (1990).

[25] T. Clackson et al., "Making Antibody Fragments Using Phage Display Libraries," *Nature*, 352, pp. 624–28 (1991).

[26] L. Osborn et al., "Direct Expression Cloning of Vascular Cell Adhesion Molecule 1, a Cytokine-induced Endothelial Protein That Binds to Lymphocytes," *Cell*, 59, pp. 1203–11 (1989).

[27] J. Devlin et al., "Random Peptide Libraries: A Source of Specific Protein Binding Molecules," *Science*, 249, pp. 400–406 (1990).

[28] J. Scott and G. Smith, "Searching for Peptide Ligands with an Epitope Library," *Science*, 249, pp. 386–90 (1990).

[29] U.S. Pat. No. 4,833,092, Geysen, "Method For Determining Mimotopes", issued May 23, 1989.

[30] S. Lichtiger and D. Present, "Preliminary Report: Cyclosporin in Treatment of Severe Active Ulcerative Colitis," *Lancet*, 336, pp. 16–19 (1990).

[31] R. Lobb et al., "Expression and Functional Characterization of a Soluble Form of Endothelial-Leukocyte Adhesion Molecule 1," *J. Immunol.*, 147(1), pp. 124–29 (1991).

[32] R. Lobb et al., "Expression and Functional Characterization of a Soluble Form of Vascular Cell Adhesion Molecule 1," *Biochem. Biophys. Res. Commun.*, 178(3), pp. 1498–1504 (1991).

[33] W. M. Abraham et al., "Cellular Markers of Inflammation in the Airways of Allergic Sheep with and without Allergen-induced Late Responses," *Am. Rev. Respir. Dis.*, 138, 1565–1571 (1988)

[34] Sambrook et al., "Polymerase Chain Reaction", *Molecular Cloning*, 3, 370–31 (1989)

[35] J. Barsoum, *DNA and Cell Biol.*, 9, 293–300 (1990)
[36] Miller et al., *J. Exp. Med.*, 178, 211 (1993)

The foregoing documents are incorporated herein by reference.

---

SEQUENCE LISTING

<160> NUMBER OF SEQ ID NOS: 16

<210> SEQ ID NO 1
<211> LENGTH: 363
<212> TYPE: DNA
<213> ORGANISM: Mus musculus
<220> FEATURE:
<221> NAME/KEY: CDS
<222> LOCATION: (1)...(363)
<220> FEATURE:
<221> NAME/KEY: misc_feature
<222> LOCATION: (1)
<223> OTHER INFORMATION: /note= "pBAG159 insert: HP1/2 heavy chain
      variable regions; amino acid 1 is Glu (E) but Gln (Q) may be
      substituted as shown in SEQ ID NO:15 and 16"

<400> SEQUENCE: 1

```
gar gtc aaa ctg cag cag tct ggg gca gag ctt gtg aag cca ggg gcc      48
Glu Val Lys Leu Gln Gln Ser Gly Ala Glu Leu Val Lys Pro Gly Ala
 1               5                  10                  15 tca gtc aag ttg tcc tgc aca gct tct ggc ttc aac att aaa gac acc      96
Ser Val Lys Leu Ser Cys Thr Ala Ser Gly Phe Asn Ile Lys Asp Thr
             20                  25                  30 tat atg cac tgg gtg aag cag agg cct gaa cag ggc ctg gag tgg att     144
Tyr Met His Trp Val Lys Gln Arg Pro Glu Gln Gly Leu Glu Trp Ile
         35                  40                  45 gga agg att gat cct gcg agt ggc gat act aaa tat gac ccg aag ttc     192
Gly Arg Ile Asp Pro Ala Ser Gly Asp Thr Lys Tyr Asp Pro Lys Phe
     50                  55                  60 cag gtc aag gcc act att aca gcg gac acg tcc tcc aac aca gcc tgg     240
Gln Val Lys Ala Thr Ile Thr Ala Asp Thr Ser Ser Asn Thr Ala Trp
 65                  70                  75                  80 ctg cag ctc agc agc ctg aca tct gag gac act gcc gtc tac tac tgt     288
Leu Gln Leu Ser Ser Leu Thr Ser Glu Asp Thr Ala Val Tyr Tyr Cys
                 85                  90                  95 gca gac gga atg tgg gta tca acg gga tat gct ctg gac ttc tgg ggc     336
Ala Asp Gly Met Trp Val Ser Thr Gly Tyr Ala Leu Asp Phe Trp Gly
            100                 105                 110 caa ggg acc acg gtc acc gtc tcc tca                                 363
Gln Gly Thr Thr Val Thr Val Ser Ser
            115                 120
```

<210> SEQ ID NO 2
<211> LENGTH: 121
<212> TYPE: PRT
<213> ORGANISM: Mus musculus

<400> SEQUENCE: 2

```
Glu Val Lys Leu Gln Gln Ser Gly Ala Glu Leu Val Lys Pro Gly Ala
 1               5                  10                  15

Ser Val Lys Leu Ser Cys Thr Ala Ser Gly Phe Asn Ile Lys Asp Thr
             20                  25                  30

Tyr Met His Trp Val Lys Gln Arg Pro Glu Gln Gly Leu Glu Trp Ile
         35                  40                  45

Gly Arg Ile Asp Pro Ala Ser Gly Asp Thr Lys Tyr Asp Pro Lys Phe
     50                  55                  60

Gln Val Lys Ala Thr Ile Thr Ala Asp Thr Ser Ser Asn Thr Ala Trp
 65                  70                  75                  80
```

```
                    -continued

Leu Gln Leu Ser Ser Leu Thr Ser Glu Asp Thr Ala Val Tyr Tyr Cys
                85                  90                  95

Ala Asp Gly Met Trp Val Ser Thr Gly Tyr Ala Leu Asp Phe Trp Gly
            100                 105                 110

Gln Gly Thr Thr Val Thr Val Ser Ser
        115                 120

<210> SEQ ID NO 3
<211> LENGTH: 318
<212> TYPE: DNA
<213> ORGANISM: Mus musculus
<220> FEATURE:
<221> NAME/KEY: CDS
<222> LOCATION: (1)...(318)
<220> FEATURE:
<221> NAME/KEY: misc_feature
<222> LOCATION: (1)
<223> OTHER INFORMATION: /note= "pBAG172 insert: HP1/2 light chain
      variable region"

<400> SEQUENCE: 3 agt att gtg atg acc cag act ccc aaa ttc ctg ctt gtt tca gca gga        48
Ser Ile Val Met Thr Gln Thr Pro Lys Phe Leu Leu Val Ser Ala Gly
  1               5                  10                  15 gac agg gtt acc ata acc tgc aag gcc agt cag agt gtg act aat gat        96
Asp Arg Val Thr Ile Thr Cys Lys Ala Ser Gln Ser Val Thr Asn Asp
                 20                  25                  30 gta gct tgg tac caa cag aag cca ggg cag tct cct aaa ctg ctg ata       144
Val Ala Trp Tyr Gln Gln Lys Pro Gly Gln Ser Pro Lys Leu Leu Ile
             35                  40                  45 tat tat gca tcc aat cgc tac act gga gtc cct gat cgc ttc act ggc       192
Tyr Tyr Ala Ser Asn Arg Tyr Thr Gly Val Pro Asp Arg Phe Thr Gly
         50                  55                  60 agt gga tat ggg acg gat ttc act ttc acc atc agc act gtg cag gct       240
Ser Gly Tyr Gly Thr Asp Phe Thr Phe Thr Ile Ser Thr Val Gln Ala
 65                  70                  75                  80 gaa gac ctg gca gtt tat ttc tgt cag cag gat tat agc tct ccg tac       288
Glu Asp Leu Ala Val Tyr Phe Cys Gln Gln Asp Tyr Ser Ser Pro Tyr
                 85                  90                  95 acg ttc gga ggg ggg acc aag ctg gag atc                               318
Thr Phe Gly Gly Gly Thr Lys Leu Glu Ile
                100                 105

<210> SEQ ID NO 4
<211> LENGTH: 106
<212> TYPE: PRT
<213> ORGANISM: Mus musculus

<400> SEQUENCE: 4

Ser Ile Val Met Thr Gln Thr Pro Lys Phe Leu Leu Val Ser Ala Gly
  1               5                  10                  15

Asp Arg Val Thr Ile Thr Cys Lys Ala Ser Gln Ser Val Thr Asn Asp
                 20                  25                  30

Val Ala Trp Tyr Gln Gln Lys Pro Gly Gln Ser Pro Lys Leu Leu Ile
             35                  40                  45

Tyr Tyr Ala Ser Asn Arg Tyr Thr Gly Val Pro Asp Arg Phe Thr Gly
         50                  55                  60

Ser Gly Tyr Gly Thr Asp Phe Thr Phe Thr Ile Ser Thr Val Gln Ala
 65                  70                  75                  80
```

```
Glu Asp Leu Ala Val Tyr Phe Cys Gln Gln Asp Tyr Ser Ser Pro Tyr
             85                  90                  95

Thr Phe Gly Gly Gly Thr Lys Leu Glu Ile
            100                 105

<210> SEQ ID NO 5
<211> LENGTH: 1347
<212> TYPE: DNA
<213> ORGANISM: Homo sapiens
<220> FEATURE:
<221> NAME/KEY: CDS
<222> LOCATION: (1)...(1338)
<220> FEATURE:
<221> NAME/KEY: VCAM-1 gene sequence
<222> LOCATION: (1)...(219)
<223> OTHER INFORMATION: This portion of the sequence corresponds,
      in part, to Exons I, II and III nucleotide sequence of Cybulsky
      et al. Proc. Nat'l. Acad. Sci. USA 88: 7861 (1991).
<220> FEATURE:
<221> NAME/KEY: Hinge regions
<222> LOCATION: (220)...(229)
<223> OTHER INFORMATION: This portion of the sequence corresponds,
      in part, to Fig. 12A in PCT/US92/02050 and represents the hinge
      region of Human IgG1 heavy chain constant region.
<220> FEATURE:
<221> NAME/KEY: Heavy chain constant region 2
<222> LOCATION: (230)...(338)
<223> OTHER INFORMATION: This portion of the sequence corresponds,
      in part, to Fig. 12A in PCT/US92/02050 and represents the heavy
      chain constat region 2 of Human IgG1 heavy chain constant region.
<220> FEATURE:
<221> NAME/KEY: Heavy chain constant region 3
<222> LOCATION: (339)...(446)
<223> OTHER INFORMATION: This portion of the sequence corresponds,
      in part, to Fig. 12A in PCT/US92/02050 and represents the heavy
      chain constat region 3 of Human IgG1 heavy chain constant region.

<400> SEQUENCE: 5 atg cct ggg aag atg gtc gtg atc ctt gga gcc tca aat ata ctt tgg     48
Met Pro Gly Lys Met Val Val Ile Leu Gly Ala Ser Asn Ile Leu Trp
 1               5                  10                  15 ata atg ttt gca gct tct caa gct ttt aaa atc gag acc acc cca gaa     96
Ile Met Phe Ala Ala Ser Gln Ala Phe Lys Ile Glu Thr Thr Pro Glu
            20                  25                  30 tct aga tat ctt gct cag att ggt gac tcc gtc tca ttg act tgc agc    144
Ser Arg Tyr Leu Ala Gln Ile Gly Asp Ser Val Ser Leu Thr Cys Ser
        35                  40                  45 acc aca ggc tgt gag tcc cca ttt ttc tct tgg aga acc cag ata gat    192
Thr Thr Gly Cys Glu Ser Pro Phe Phe Ser Trp Arg Thr Gln Ile Asp
    50                  55                  60 agt cca ctg aat ggg aag gtg acg aat gag ggg acc aca tct acg ctg    240
Ser Pro Leu Asn Gly Lys Val Thr Asn Glu Gly Thr Thr Ser Thr Leu
65                  70                  75                  80 aca atg aat cct gtt agt ttt ggg aac gaa cac tct tac ctg tgc aca    288
Thr Met Asn Pro Val Ser Phe Gly Asn Glu His Ser Tyr Leu Cys Thr
                85                  90                  95 gca act tgt gaa tct agg aaa ttg gaa aaa gga atc cag gtg gag atc    336
Ala Thr Cys Glu Ser Arg Lys Leu Glu Lys Gly Ile Gln Val Glu Ile
            100                 105                 110 tac tct ttt cct aag gat cca gag att cat ttg agt ggc cct ctg gag    384
Tyr Ser Phe Pro Lys Asp Pro Glu Ile His Leu Ser Gly Pro Leu Glu
        115                 120                 125 gct ggg aag ccg atc aca gtc aag tgt tca gtt gct gat gta tac cca    432
Ala Gly Lys Pro Ile Thr Val Lys Cys Ser Val Ala Asp Val Tyr Pro
    130                 135                 140
```

-continued

| | | |
|---|---|---|
| ttt gac agg ctg gag ata gac tta ctg aaa gga gat cat ctc atg aag<br>Phe Asp Arg Leu Glu Ile Asp Leu Leu Lys Gly Asp His Leu Met Lys<br>145                    150                    155                    160 | 480 |
| agt cag gaa ttt ctg gag gat gca gac agg aag tcc ctg gaa acc aag<br>Ser Gln Glu Phe Leu Glu Asp Ala Asp Arg Lys Ser Leu Glu Thr Lys<br>                165                    170                    175 | 528 |
| agt ttg gaa gta acc ttt act cct gtc att gag gat att gga aaa gtt<br>Ser Leu Glu Val Thr Phe Thr Pro Val Ile Glu Asp Ile Gly Lys Val<br>                180                    185                    190 | 576 |
| ctt gtt tgc cga gct aaa tta cac att gat gaa atg gat tct gtg ccc<br>Leu Val Cys Arg Ala Lys Leu His Ile Asp Glu Met Asp Ser Val Pro<br>                    195                    200                    205 | 624 |
| aca gta agg cag gct gta aaa gaa ttg caa gtc gac aaa act cac aca<br>Thr Val Arg Gln Ala Val Lys Glu Leu Gln Val Asp Lys Thr His Thr<br>210                    215                    220 | 672 |
| tgc cca ccg tgc cca gca cct gaa ctc ctg ggg gga ccg tca gtc ttc<br>Cys Pro Pro Cys Pro Ala Pro Glu Leu Leu Gly Gly Pro Ser Val Phe<br>225                    230                    235                    240 | 720 |
| ctc ttc ccc cca aaa ccc aag gac acc ctc atg atc tcc cgg acc cct<br>Leu Phe Pro Pro Lys Pro Lys Asp Thr Leu Met Ile Ser Arg Thr Pro<br>                245                    250                    255 | 768 |
| gag gtc aca tgc gtg gtg gtg gac gtg agc cac gaa gac cct gag gtc<br>Glu Val Thr Cys Val Val Val Asp Val Ser His Glu Asp Pro Glu Val<br>                    260                    265                    270 | 816 |
| aag ttc aac tgg tac gtg gac ggc gtg gag gtg cat aat gcc aag aca<br>Lys Phe Asn Trp Tyr Val Asp Gly Val Glu Val His Asn Ala Lys Thr<br>                275                    280                    285 | 864 |
| aag ccg cgg gag gag cag tac aac agc acg tac cgg gtg gtc agc gtc<br>Lys Pro Arg Glu Glu Gln Tyr Asn Ser Thr Tyr Arg Val Val Ser Val<br>290                    295                    300 | 912 |
| ctc acc gtc ctg cac cag gac tgg ctg aat ggc aag gag tac aag tgc<br>Leu Thr Val Leu His Gln Asp Trp Leu Asn Gly Lys Glu Tyr Lys Cys<br>305                    310                    315                    320 | 960 |
| aag gtc tcc aac aaa gcc ctc cca gcc ccc atc gag aaa acc atc tcc<br>Lys Val Ser Asn Lys Ala Leu Pro Ala Pro Ile Glu Lys Thr Ile Ser<br>                325                    330                    335 | 1008 |
| aaa gcc aaa ggg cag ccc cga gaa cca cag gtg tac acc ctg ccc cca<br>Lys Ala Lys Gly Gln Pro Arg Glu Pro Gln Val Tyr Thr Leu Pro Pro<br>                    340                    345                    350 | 1056 |
| tcc cgg gat gag ctg acc aag aac cag gtc agc ctg acc tgc ctg gtc<br>Ser Arg Asp Glu Leu Thr Lys Asn Gln Val Ser Leu Thr Cys Leu Val<br>355                    360                    365 | 1104 |
| aaa ggc ttc tat ccc agc gac atc gcc gtg gag tgg gag agc aat ggg<br>Lys Gly Phe Tyr Pro Ser Asp Ile Ala Val Glu Trp Glu Ser Asn Gly<br>370                    375                    380 | 1152 |
| cag ccg gag aac aac tac aag acc acg cct ccc gtg ctg gac tcc gac<br>Gln Pro Glu Asn Asn Tyr Lys Thr Thr Pro Pro Val Leu Asp Ser Asp<br>385                    390                    395                    400 | 1200 |
| ggc tcc ttc ttc ctc tac agc aag ctc acc gtg gac aag agc agg tgg<br>Gly Ser Phe Phe Leu Tyr Ser Lys Leu Thr Val Asp Lys Ser Arg Trp<br>                405                    410                    415 | 1248 |
| cag cag ggg aac gtc ttc tca tgc tcc gtg atg cat gag gct ctg cac<br>Gln Gln Gly Asn Val Phe Ser Cys Ser Val Met His Glu Ala Leu His<br>                    420                    425                    430 | 1296 |
| aac cac tac acg cag aag agc ctc tcc ctg tct ccg ggt aaa<br>Asn His Tyr Thr Gln Lys Ser Leu Ser Leu Ser Pro Gly Lys<br>435                    440                    445 | 1338 |
| tgagtgcgg | 1347 |

```
<210> SEQ ID NO 6
<211> LENGTH: 24
<212> TYPE: DNA
<213> ORGANISM: Homo sapiens
<220> FEATURE:
<221> NAME/KEY: CDS
<222> LOCATION: (6)...(23)

<400> SEQUENCE: 6 tcgtc gac aaa act cac aca tgc c                                 24
      Asp Lys Thr His Thr Cys
        1               5

<210> SEQ ID NO 7
<211> LENGTH: 24
<212> TYPE: DNA
<213> ORGANISM: Artificial Sequence
<220> FEATURE:
<223> OTHER INFORMATION: primer for PCR

<400> SEQUENCE: 7
gtaaatgagt gcggcggccg ccaa                                      24

<210> SEQ ID NO 8
<211> LENGTH: 115
<212> TYPE: DNA
<213> ORGANISM: Artificial Sequence
<220> FEATURE:
<223> OTHER INFORMATION: synthetic polylinker sequence

<400> SEQUENCE: 8
gcggccgcgg tccaaccacc aatctcaaag cttggtaccc gggaattcag atctgcagca     60
tgctcgagct ctagatatcg attccatgga tcctcacatc ccaatccgcg gccgc         115

<210> SEQ ID NO 9
<211> LENGTH: 41
<212> TYPE: DNA
<213> ORGANISM: Homo sapiens
<220> FEATURE:
<221> NAME/KEY: CDS
<222> LOCATION: (21)...(41)

<400> SEQUENCE: 9
gagctcgagg cggccgcacc atg cct ggg aag atg gtc gtg               41
                     Met Pro Gly Lys Met Val Val
                       1               5

<210> SEQ ID NO 10
<211> LENGTH: 23
<212> TYPE: DNA
<213> ORGANISM: Homo sapiens

<400> SEQUENCE: 10
aagtcgactt gcaattcttt tac                                       23

<210> SEQ ID NO 11
<211> LENGTH: 14
<212> TYPE: DNA
<213> ORGANISM: Artificial Sequence
<220> FEATURE:
<223> OTHER INFORMATION: phosphorylated oligonucleotide

<400> SEQUENCE: 11
tcgacgcggc cgcg                                                 14
```

<210> SEQ ID NO 12
<211> LENGTH: 446
<212> TYPE: PRT
<213> ORGANISM: Homo sapiens

<400> SEQUENCE: 12

Met Pro Gly Lys Met Val Val Ile Leu Gly Ala Ser Asn Ile Leu Trp
1               5                   10                  15

Ile Met Phe Ala Ala Ser Gln Ala Phe Lys Ile Glu Thr Thr Pro Glu
            20                  25                  30

Ser Arg Tyr Leu Ala Gln Ile Gly Asp Ser Val Ser Leu Thr Cys Ser
        35                  40                  45

Thr Thr Gly Cys Glu Ser Pro Phe Phe Ser Trp Arg Thr Gln Ile Asp
    50                  55                  60

Ser Pro Leu Asn Gly Lys Val Thr Asn Glu Gly Thr Thr Ser Thr Leu
65                  70                  75                  80

Thr Met Asn Pro Val Ser Phe Gly Asn Glu His Ser Tyr Leu Cys Thr
                85                  90                  95

Ala Thr Cys Glu Ser Arg Lys Leu Glu Lys Gly Ile Gln Val Glu Ile
            100                 105                 110

Tyr Ser Phe Pro Lys Asp Pro Glu Ile His Leu Ser Gly Pro Leu Glu
        115                 120                 125

Ala Gly Lys Pro Ile Thr Val Lys Cys Ser Val Ala Asp Val Tyr Pro
    130                 135                 140

Phe Asp Arg Leu Glu Ile Asp Leu Leu Lys Gly Asp His Leu Met Lys
145                 150                 155                 160

Ser Gln Glu Phe Leu Glu Asp Ala Asp Arg Lys Ser Leu Glu Thr Lys
                165                 170                 175

Ser Leu Glu Val Thr Phe Thr Pro Val Ile Glu Asp Ile Gly Lys Val
            180                 185                 190

Leu Val Cys Arg Ala Lys Leu His Ile Asp Glu Met Asp Ser Val Pro
        195                 200                 205

Thr Val Arg Gln Ala Val Lys Glu Leu Gln Val Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

```
Gln Pro Glu Asn Asn Tyr Lys Thr Thr Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 13
<211> LENGTH: 6
<212> TYPE: PRT
<213> ORGANISM: Artificial Sequence
<220> FEATURE:
<223> OTHER INFORMATION: synthetically generated peptide

<400> SEQUENCE: 13

Asp Lys Thr His Thr Cys
  1               5

<210> SEQ ID NO 14
<211> LENGTH: 7
<212> TYPE: PRT
<213> ORGANISM: Homo sapiens

<400> SEQUENCE: 14

Met Pro Gly Lys Met Val Val
  1               5

<210> SEQ ID NO 15
<211> LENGTH: 363
<212> TYPE: DNA
<213> ORGANISM: Mus musculus
<220> FEATURE:
<221> NAME/KEY: CDS
<222> LOCATION: (1)...(363)
<220> FEATURE:
<221> NAME/KEY: misc_feature
<222> LOCATION: (1)
<223> OTHER INFORMATION: /note= "pBAG159 insert: HP1/2 heavy chain
      variable regions

<400> SEQUENCE: 15 car gtc aaa ctg cag cag tct ggg gca gag ctt gtg aag cca ggg gcc        48
Gln Val Lys Leu Gln Gln Ser Gly Ala Glu Leu Val Lys Pro Gly Ala
  1               5                   10                  15 tca gtc aag ttg tcc tgc aca gct tct ggc ttc aac att aaa gac acc        96
Ser Val Lys Leu Ser Cys Thr Ala Ser Gly Phe Asn Ile Lys Asp Thr
                20                  25                  30 tat atg cac tgg gtg aag cag agg cct gaa cag ggc ctg gag tgg att       144
Tyr Met His Trp Val Lys Gln Arg Pro Glu Gln Gly Leu Glu Trp Ile
            35                  40                  45 gga agg att gat cct gcg agt ggc gat act aaa tat gac ccg aag ttc       192
Gly Arg Ile Asp Pro Ala Ser Gly Asp Thr Lys Tyr Asp Pro Lys Phe
        50                  55                  60 cag gtc aag gcc act att aca gcg gac acg tcc tcc aac aca gcc tgg       240
Gln Val Lys Ala Thr Ile Thr Ala Asp Thr Ser Ser Asn Thr Ala Trp
 65                  70                  75                  80 ctg cag ctc agc agc ctg aca tct gag gac act gcc gtc tac tac tgt       288
Leu Gln Leu Ser Ser Leu Thr Ser Glu Asp Thr Ala Val Tyr Tyr Cys
                85                  90                  95
```

-continued

```
gca gac gga atg tgg gta tca acg gga tat gct ctg gac ttc tgg ggc    336
Ala Asp Gly Met Trp Val Ser Thr Gly Tyr Ala Leu Asp Phe Trp Gly
            100                 105                 110 caa ggg acc acg gtc acc gtc tcc tca                                363
Gln Gly Thr Thr Val Thr Val Ser Ser
        115                 120
```

<210> SEQ ID NO 16
<211> LENGTH: 121
<212> TYPE: PRT
<213> ORGANISM: Mus musculus

<400> SEQUENCE: 16

```
Gln Val Lys Leu Gln Gln Ser Gly Ala Glu Leu Val Lys Pro Gly Ala
 1               5                  10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Ser Gly Asp Thr Lys Tyr Asp Pro Lys Phe
    50                  55                  60

Gln Val Lys Ala Thr Ile Thr Ala Asp Thr Ser Ser Asn Thr Ala Trp
65                  70                  75                  80

Leu Gln Leu Ser Ser Leu Thr Ser Glu Asp Thr Ala Val Tyr Tyr Cys
                85                  90                  95

Ala Asp Gly Met Trp Val Ser Thr Gly Tyr Ala Leu Asp Phe Trp Gly
            100                 105                 110

Gln Gly Thr Thr Val Thr Val Ser Ser
        115                 120
```

The invention claimed is:

1. A method for the treatment of inflammatory bowel disease, the method comprising: administering to a mammal suffering from inflammatory bowel disease a composition comprising a soluble fibronectin polypeptide fragment, wherein the fragment consists of amino acid sequence EILDV (SEQ ID NO:17) in an amount effective to treat inflammatory bowel disease.

2. The method according to claim 1, wherein the fibronectin polypeptide fragment is a component of a chimeric molecule.

3. The method according to claim 2, wherein the chimeric molecule further comprises a toxin moiety.

4. The method according to claim 1, wherein the mammal is a human.

5. The method according to claim 1, wherein the mammal suffers from ulcerative colitis.

6. The method according to claim 1, wherein the mammal suffers from Crohn's Disease.

7. The method of claim 1, wherein the composition is administered intravenously.

8. The method of claim 1, wherein the composition is administered during an acute flareup of the inflammatory bowel disease.

9. The method of claim 1, wherein the composition further comprises an anti-ELAM-1 antibody, an anti-ICAM-1 antibody, an anti-VCAM-1 antibody, an anti-LFA-1 antibody, an anti-CD18 antibody, or any combination of such antibodies.

* * * * *